(12) United States Patent
Rasor et al.

(10) Patent No.: US 9,913,956 B2
(45) Date of Patent: Mar. 13, 2018

(54) EVERTING DEVICE AND METHOD FOR TRACHEOSTOMY

(71) Applicants: Julia Suzanne Rasor, San Diego, CA (US); Ned Shaurer Rasor, Dayton, OH (US)

(72) Inventors: Julia Suzanne Rasor, San Diego, CA (US); Ned Shaurer Rasor, Dayton, OH (US)

( * ) Notice: Subject to any disclaimer, the term of this patent is extended or adjusted under 35 U.S.C. 154(b) by 693 days.

(21) Appl. No.: 14/020,878

(22) Filed: Sep. 8, 2013

(65) Prior Publication Data
US 2014/0174449 A1 Jun. 26, 2014

Related U.S. Application Data

(62) Division of application No. 12/857,493, filed on Aug. 16, 2010, now abandoned.

(60) Provisional application No. 61/274,478, filed on Aug. 18, 2009, provisional application No. 61/280,409, filed on Nov. 4, 2009.

(51) Int. Cl.
*A61M 16/04* (2006.01)
*A61B 17/34* (2006.01)

(52) U.S. Cl.
CPC ..... *A61M 16/0472* (2013.01); *A61B 17/3415* (2013.01); *A61M 16/0488* (2013.01)

(58) Field of Classification Search
CPC ............. A61M 16/04; A61M 16/0465; A61M 16/0472; A61M 16/0427; A61M 16/0488; A61M 25/0119; A61M 25/0662; A61M 16/0429; A61M 16/0402; A61B 17/34; A61B 17/3415; A61B 2017/3435; A61B 10/023
USPC ............ 128/207.29, 207.15, 207.14, 200.26; 604/104, 163, 171, 264, 271
See application file for complete search history.

(56) References Cited

U.S. PATENT DOCUMENTS

| | | | | | |
|---|---|---|---|---|---|
| 5,993,427 | A | * | 11/1999 | Rolland | A61M 25/0119 604/271 |
| 7,169,129 | B2 | * | 1/2007 | Gooden | A61M 16/0472 128/207.29 |
| 2001/0044595 | A1 | * | 11/2001 | Reydel | A61F 2/95 604/98.02 |
| 2004/0035432 | A1 | * | 2/2004 | Gostelow | A61M 16/0429 128/207.29 |
| 2004/0097957 | A1 | * | 5/2004 | Jaker | A61F 2/1664 606/107 |
| 2007/0123798 | A1 | * | 5/2007 | Rahamimov | A61B 1/00135 600/564 |

(Continued)

*Primary Examiner* — Todd J Scherbel
*Assistant Examiner* — Elliot S Ruddie
(74) *Attorney, Agent, or Firm* — Jill L. Robinson

(57) ABSTRACT

The invention is an integrated device and improved method for percutaneous placement of a tracheostomy tube into a patient which includes a film sheath everted from a pusher moved through a guide that is positioned over an incision site in a patient's neck. The pusher moves through an incision, which may be preexisting or created by the device, into the patient's trachea, laying down the film sheath as it advances. The film and pusher may effect blunt dissection of the patient's tissue, and the device may optionally include a blade(s), needle or other cutting tool and/or the tracheostomy tube itself so that the tracheostomy can be completed with fewer procedural steps and surgical instruments.

11 Claims, 25 Drawing Sheets

(56) References Cited

U.S. PATENT DOCUMENTS

2007/0198074 A1\* 8/2007 Dann ............... A61B 17/00234
                                                    623/1.11
2008/0195226 A1\* 8/2008 Williams ................ A61F 2/04
                                                    623/23.67
2010/0069852 A1\* 3/2010 Kelley ................ A61F 2/2436
                                                    604/264

\* cited by examiner

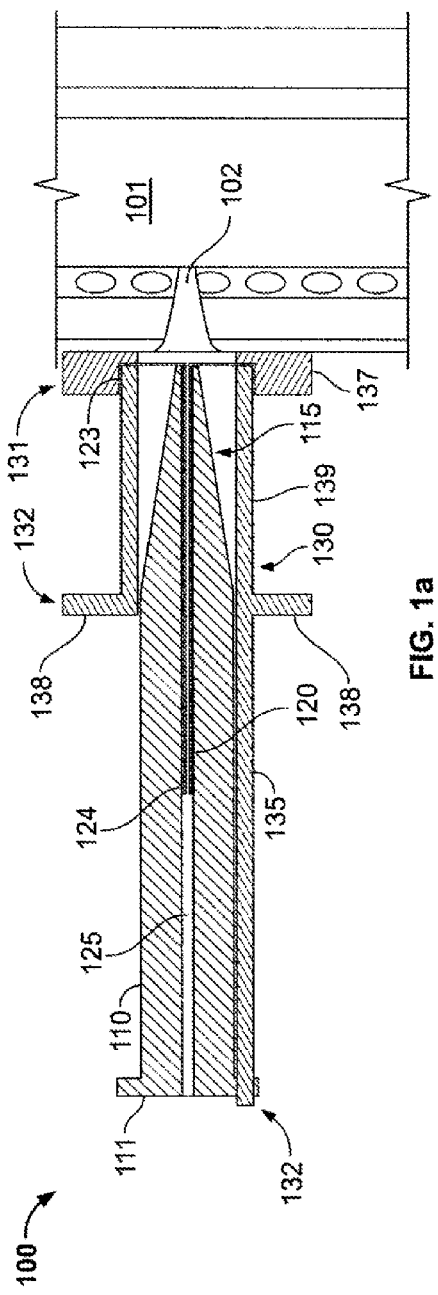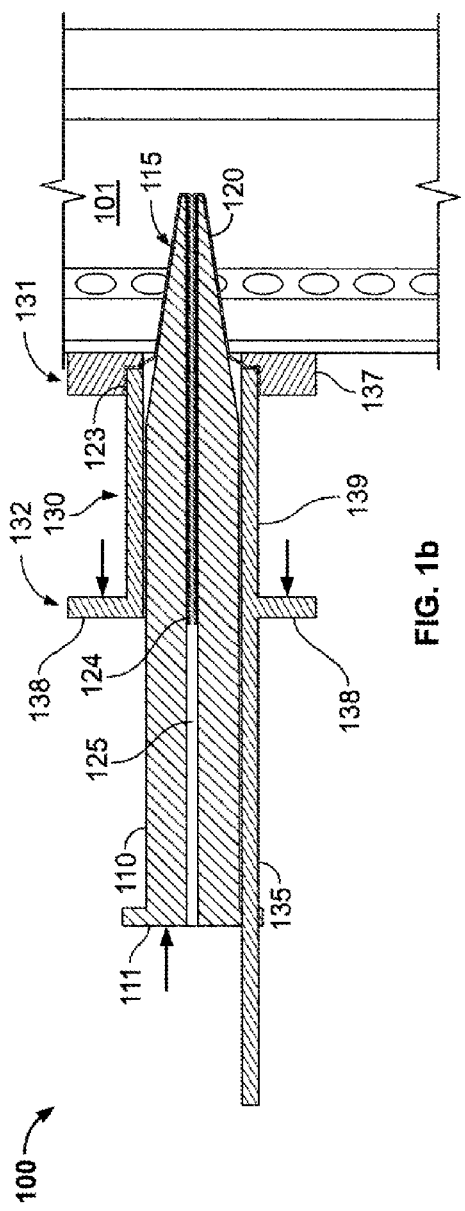

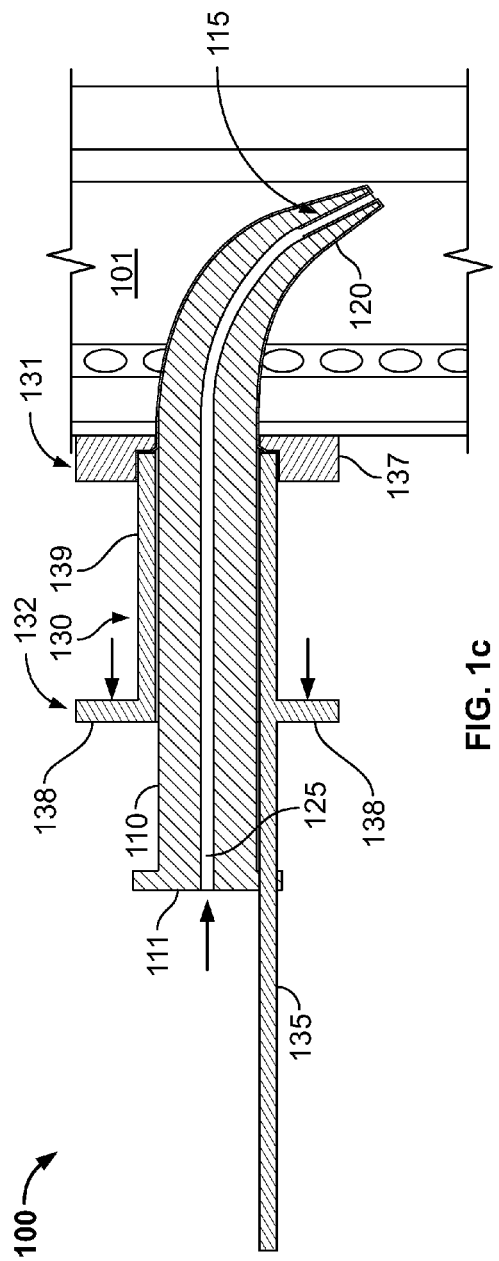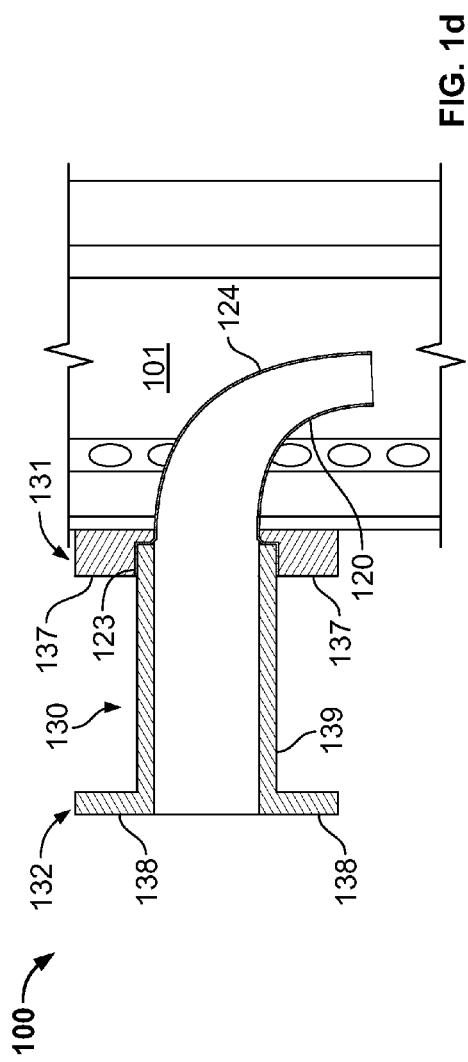

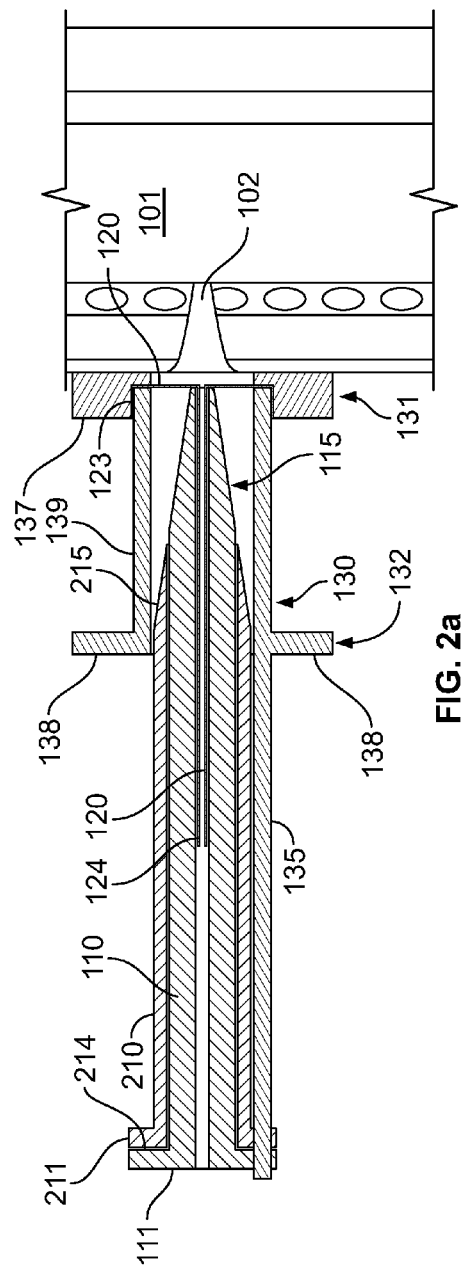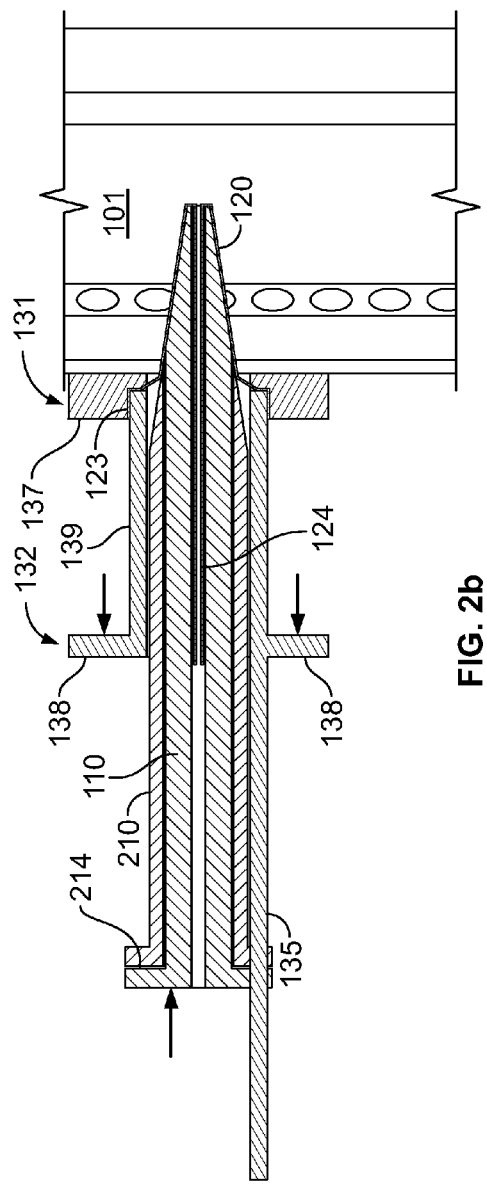
FIG. 2a
FIG. 2b

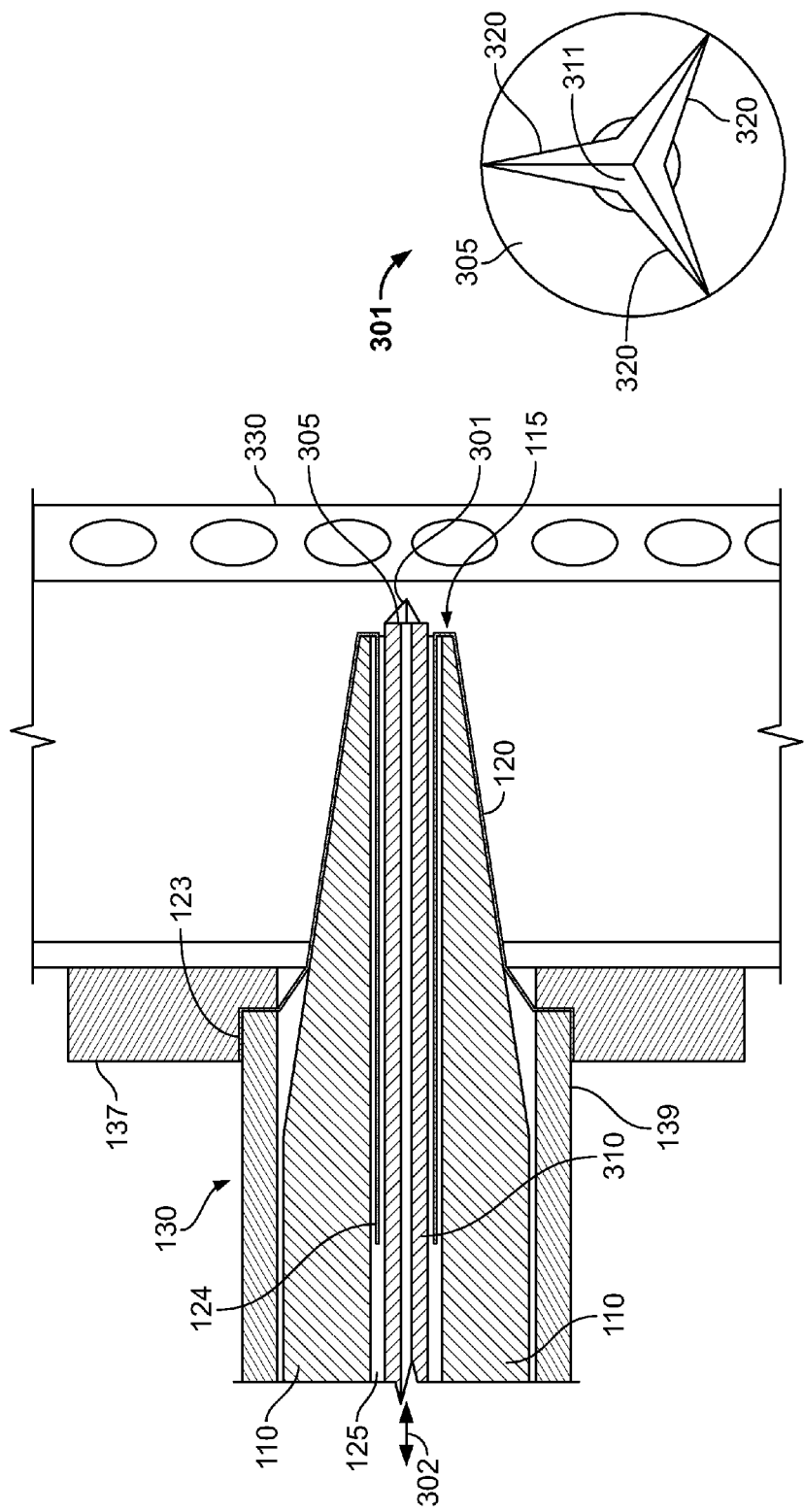

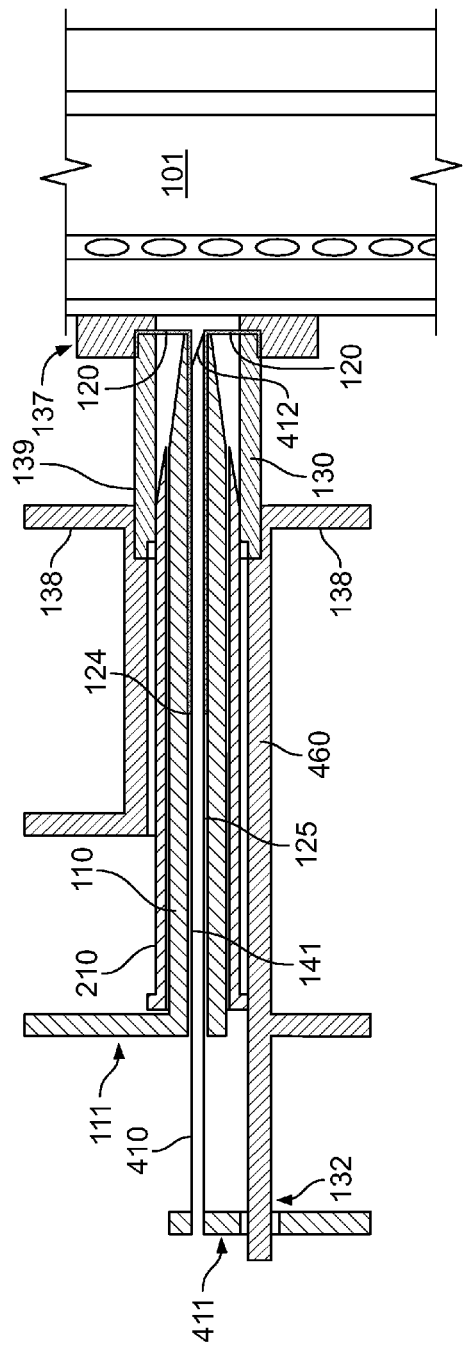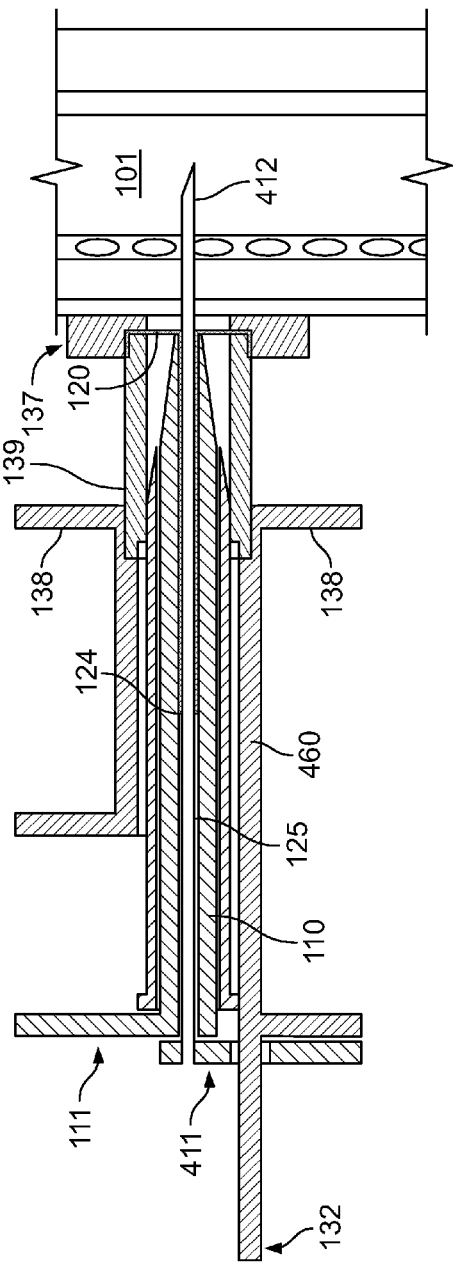

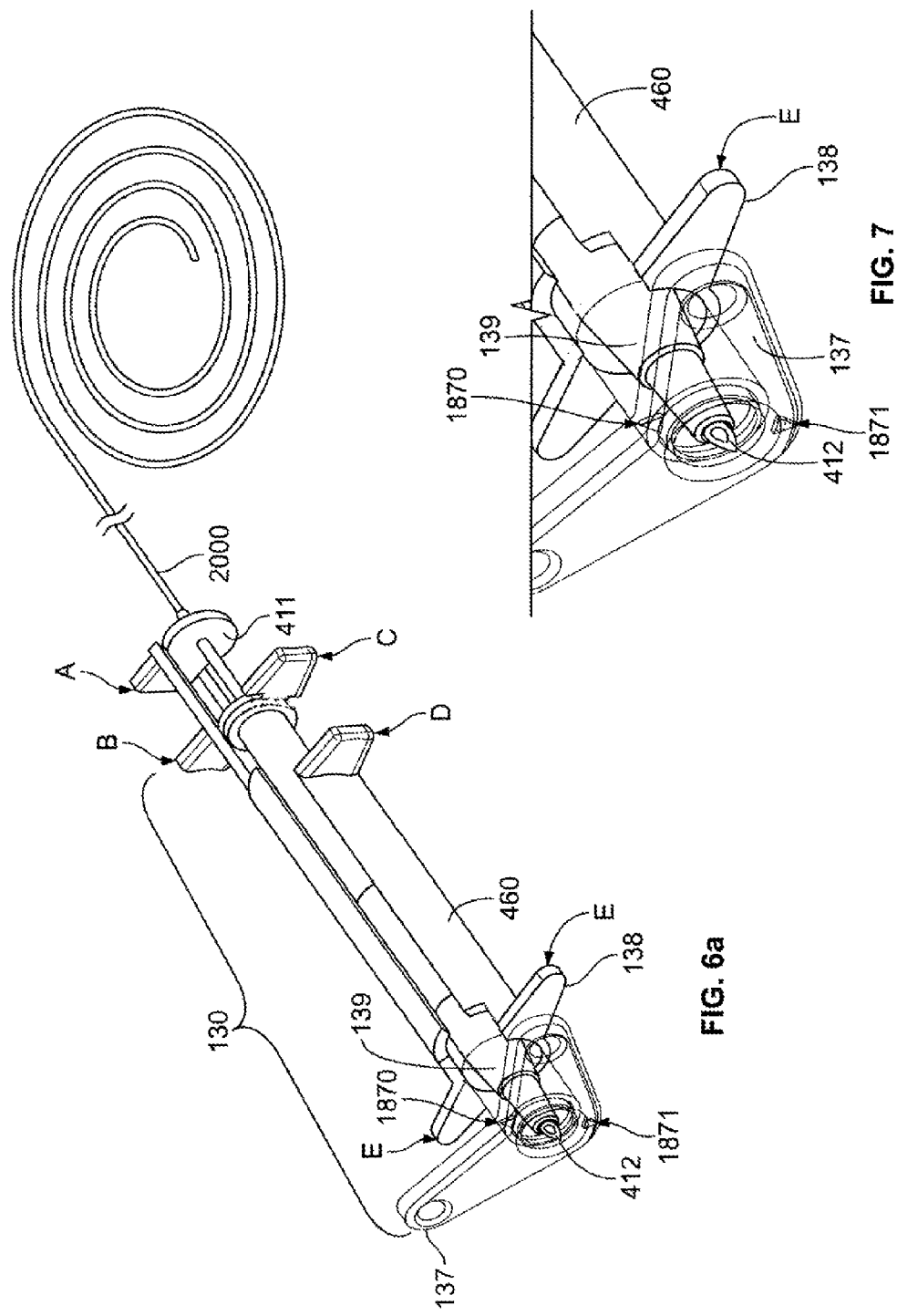

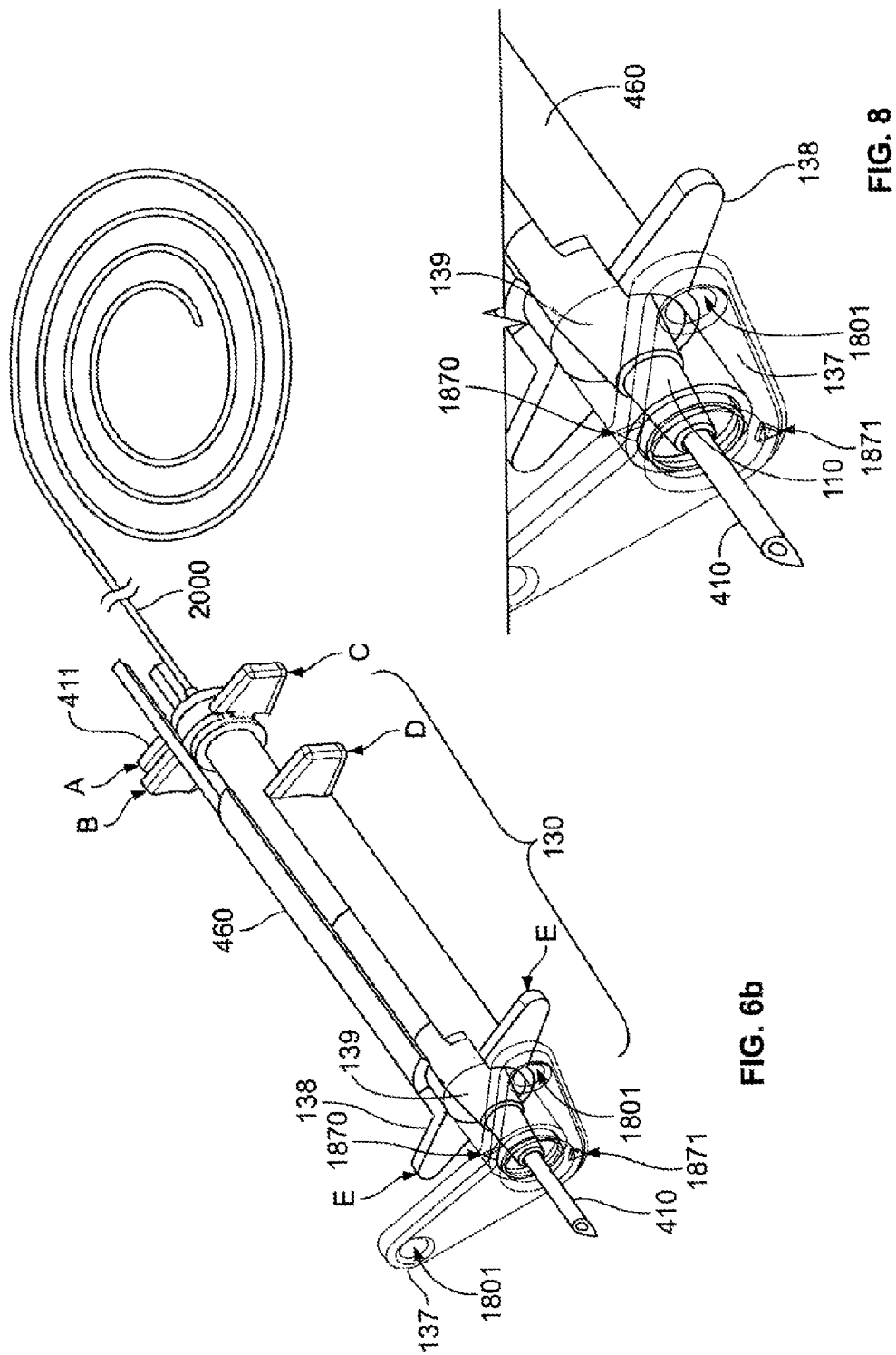

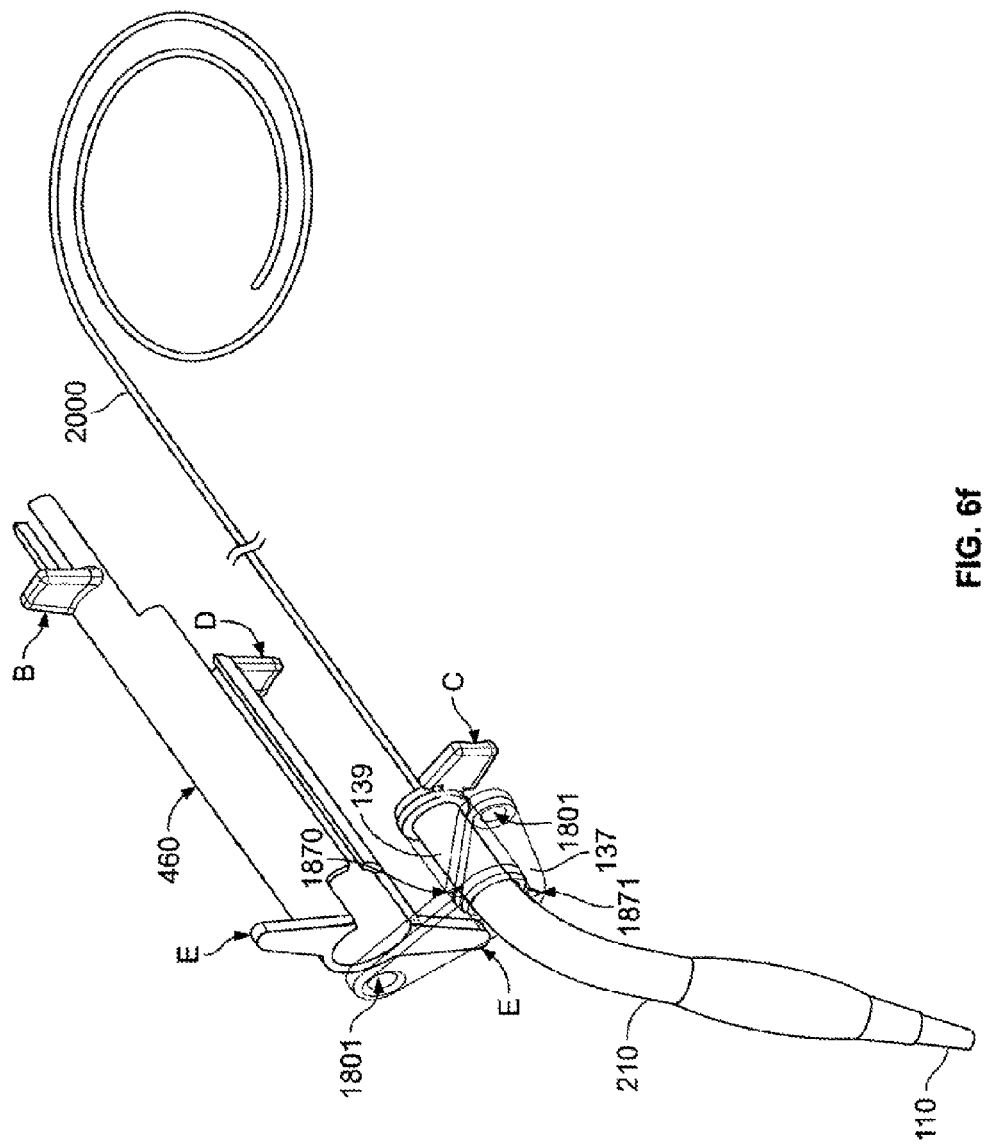

EVERTING DEVICE AND METHOD FOR TRACHEOSTOMY

BACKGROUND OF THE INVENTION

The invention relates to an improved method and related devices for percutaneous placement of airway tubes into the tracheas of living bodies, a procedure known as a tracheostomy, and subsequent supportive maintenance tracheostomy.

Tracheostomies are the most common surgical procedure performed on critically ill patients. The procedure involves multiple steps to create and dilate a stoma and insert a tracheostomy tube, each additional step creating the possibility for error. Standard dilators, such as the BLUE RHINO manufactured by Cook Critical Care, and serial dilators, are inserted with a substantial, axially-inward force to dilate the patient's tissue, which, in addition to requiring significant physical strength on the part of the surgeon, may result in surgery-related complications such as bleeding; perforation of the adjacent vasculature, esophagus, and thyroid; pneumothorax and pneumomediastinum; subcutaneous and mediastinal emphysema; cartilage fractures; and suprastomal collapse. Further, dilators drag against the patient's tissue with a shear force and considerable friction, causing tissue trauma resulting in pain, slow healing, as well as, potentially, dysphagia, extensive scarring and disfiguration. Finally, insertion of a dilator may cause infection as a result of dragging or "tracking" microbes into the trachea from the skin of the entry site or from subcutaneous layers.

After the patient's tissues are dilated, insertion of a standard tracheostomy tube, such as the SHILEY manufactured by Covidien, creates a similar shear force and friction, with the same potential for complications, as the insertion of a dilator. Additionally, while in use, the tracheostomy tube can create additional complications such as tissue erosion, fibrotic, scar and granulation tissue formation and necrosis, which can result in tracheal stenosis necessitating surgical repair. Also, the interior of the trachea includes a layer of potentially infectious material known as biofilm. Biofilm may adhere to and build up on the tracheostomy tube leading to device and airway bacterial colonization, subsequent local infection, and, finally, systemic infection such as the frequent and often fatal complication of ventilator-associated pneumonia.

It is an object of this invention to simplify the procedure and reduce the number of components and steps required for tracheostomy.

It is a further object of this invention to provide a device and method that require less axial force to dilate patient tissue and less shear and frictional force to insert an airway into the patient's trachea.

It is a further object of this invention to provide a device and method that reduce the potential of infection and other complications associated with tracheostomy.

It is a further object of this invention to provide a device and method that reduce tissue trauma such as rubbing frictional and pressure necrosis, scarring, and granulation produced by a tracheostomy tube while in situ in a trachea.

BRIEF SUMMARY OF THE INVENTION

The present invention utilizes everting technology, in combination with novel means for placement and maintenance of airway tubes, to simplify tracheostomy, reduce trauma to the intervening and adjacent tissue and minimize the potential for microbial infection. While it is anticipated that the invention would be used for tracheostomy, the claimed device could also be used for cricothyrotomy.

Everting is the laying down of a thin-walled "film" sheath along the tissue entrance path wall during advancement of a placement device, somewhat like tank treads being laid down along the ground. The film sheath is pre-loaded inside a placement device and as the film sheath emerges it everts, with the inside of the film sheath becoming the outside. The extremely thin-walled film sheath is made of a biomaterial that is lubricious, strong, flexible, and resilient. Use of such an everting film sheath virtually eliminates the drag, shear force, and friction generally associated with placement, maintenance and removal of standard tracheostomy devices, minimizing trauma and the potential for microbial infection. The chance of infection is further reduced by appropriate selection of biomaterial to reduce or eliminate biofilm buildup.

An everting film placement device may stand-alone or be integrated with a tracheostomy tube. If stand-alone, the device places and secures the protective film sheath into a patient's trachea to facilitate subsequent placement, maintenance and removal of a standard tracheostomy tube. If the placement device and tracheostomy tube are integrated, the device, simultaneously with the placement of the film sheath, places and secures the tracheostomy tube into the patient's trachea. The device can be used to place film, alone or in combination with the tracheostomy tube, into the trachea through an incision, which could include a pre-existing stoma or a new tracheostomy site created by conventional surgical procedures, blunt dissection or other means. Alternatively, the device can include a cutting means and/or other features that allow for percutaneous placement of the film and device. In particular, the everting of the film sheath may provide a means of blunt dissection which spreads and dilates the tissue.

BRIEF DESCRIPTION OF THE DRAWINGS

FIGS. 2 *a-b* show an embodiment of the current invention suitable for placing film and an integrated tracheostomy tube into an existing stoma and illustrate the method steps for placement of the film and tracheostomy tube FIG. 3 shows an embodiment of the current invention including a cutting means.

FIG. 4 shows the detail of a preferred embodiment of the cutting means.

FIG. 7 shows a detail of the embodiment and step shown in FIG. 6*a*.

FIG. 8 shows a detail of the embodiment and step shown in FIG. 6*b*

DETAILED DESCRIPTION OF THE INVENTION

Figure 1E:
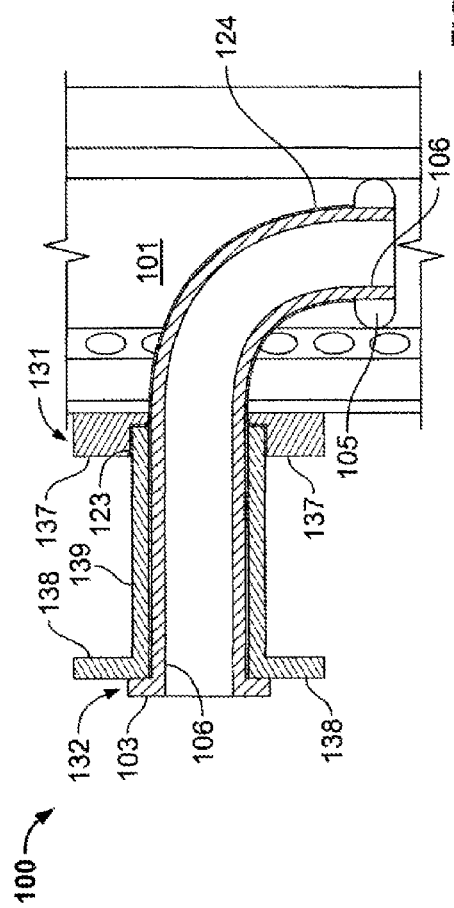
FIGS. 1 *a-f* show an embodiment of the current invention suitable for placing film into an existing stoma and illustrate the method steps for placement of the film and a conventional tracheostomy tube, and their subsequent removal.

The everting placement device of the invention, shown with various modifications in the figures includes a pushing means, which may comprise a pusher 110 or be integrated with another component, a guide 130, which is positioned and held at the appropriate location on the neck of the patient, and a first everting film sheath 120.

The pusher 110 has a proximal end 111 and a tapered distal nose 115 through which a longitudinal lumen 125 or other storage space opens. The pusher 110 is preferably flexible and pre-formed to be curved so as to allow the pusher 110 to curve caudally into the trachea 101.

The guide 130 includes connector means, which may be a tube-like connector 139 structure as shown, with a distal end 131 and proximal end 132, and also preferably includes an extension 135 or stand-off guide 460 for supporting the pusher 110. The guide also preferably includes a flange 137 that may be positioned at the appropriate location on the patient's neck and that is shaped to conform to the topography of that location. The flange 137 may be held to the patient's neck using a strap or other conventional means, is preferably v-shaped and is made of a clear material to facilitate proper placement. The connector means should be adapted for attachment to conventional ventilator tubing (not shown). The guide 130 also preferably includes finger rests 138 similar to those of a syringe. The finger rests 138 may be extensions from the connector 139, or alternatively from the extension 135 or stand-off guide 460. The outwardly facing portion of the flange 137 may also include upper and lower guide marks 1870, 1871 suitable for easy alignment with corresponding marks on the patient's neck or on a locator strip 1910 to ensure correct placement of the guide 130 using methods and devices further described below.

Alternative embodiments of the guide are possible provided certain functions are retained. There must be an external element or elements like the flange 137 near the neck of the patient, such as a ring or similar structure, to which the distal end 123 of the film sheath 120 is attached so as to absorb the force necessary to keep the distal end 123 stationary and to keep the everted portion of the film from moving while the stored portion is being deployed. There must be a connector means to connect the tracheal tube to ventilator tubing after the tracheal tube has been inserted into the patient and the film sheath. Additionally, if the pusher 110 is flexible, it preferably must be maintained by the guide in a nominally straight or otherwise axially movable configuration so as to allow a nominally axial force to be applied during use. Persons of ordinary skill in the art will appreciate that a number of alternatives, including tube-like structures that only partly enclose the pusher and guides employing slits and/or are curved, could be designed. However, it should be noted that if the pusher 110 is initially curved with the right nominal curvature for entering the trachea, the pusher 110 could be used to place the film sheath 120 in the trachea by hand using a caudally arcing motion without being maintained in a straight position or requiring any guide other than a ring or other short structure used as the connector means, positioned at the appropriate point on the patient's neck. Finally, the structure of the guide should preferably be such that, when in use, equal and opposite axial forces are applied to the guide 130 and to the pusher 110 in order to minimize the axial placement force applied to the patient's tissue during the placement process.

The film sheath 120 is composed of a highly flexible and high strength polymer film, such as skived PTFE D/W 200, a modified homopolymer PTFE manufactured by DeWAL Industries, that is generally inelastic, biocompatible and resists adhesion of bodily elements, tissue and potentially infectious contaminating material such as biofilm. Such film has been used in catheter devices. The distal end 123 of the film sheath 120 initially extends out from the lumen 125 opening formed in the tapered distal nose 115 of the pusher 110 and may be attached to the guide 130. Such attachment may be effected by permanently affixing the distal end 123 of the film sheath 120 to the appropriate portion of the guide 130 or by trapping the distal end 123 of the film sheath 120 between appropriate components of the guide 130 such as between the connector 139 and the flange 137. The remaining bulk of the film sheath 120 is initially stored inside the lumen 125. The proximal end 124 of the film sheath 120 may be free.

The embodiment shown in FIG. 1 is suitable for use in patients with a stoma 102 formed by conventional means and either already existing or newly created at the time the device 100 is to be used. It will be understood that normal surgical procedures would be followed in the usage of all of the embodiments of the device described; for example, if appropriate, the patient's tissue would be properly prepped for sterile surgery and numbed by local anesthetic before beginning the procedure. Initially, in a preferred embodiment, the flexible pusher 110 is constrained to be straight by the guide 130, which includes an attached extension 135.

To place the film sheath 120 through the stoma 102 into the tracheal lumen 101 the pusher 110 can be advanced into the guide 130 by means of an attached handle, not shown. Preferably, however, force is applied controllably, expeditiously and reproducibly to the proximal end 111 of the pusher 110 by means of the operator's thumb, with the forefinger and middle finger placed on the finger rests 138 of the guide 130, which are preferably located on the extension 135 but which may instead extend from the connector 139, as indicated in FIG. 1b, in the manner for operation of a hypodermic syringe.

As the pusher 110 is advanced, the film sheath 120 everts from the lumen 125 of the pusher 110, through the opening in the nose 115 and radially across the tip of the nose 115, to cover the exterior of the pusher 110. In this way the pusher 110 is advanced into the stoma 102 with essentially no axial force applied to the patient's tissue that can distort and damage tissue structures, such as the pretracheal tissues, tracheal cartilage and anterior and posterior tracheal wall, and structures distal to the distal tracheal wall such as the esophagus and adjacent vasculature. The stoma 102 is dilated radially from its initial relaxed or partially healed diameter to the full diameter required for the tracheal tube as the tapered distal nose 115 of the pusher 110 advances through the film sheath 120, again with essentially no substantial axial force applied to the patient's tissue.

As the pusher 110 emerges from the distal end 131 of the guide 130 into the stoma 102 and trachea 101, it curves caudally into the tracheal lumen, as shown in FIG. 1c, which may be as a result of the pre-formed, memory curvature built into the flexible pusher 110 during its manufacture. If the film-covered nose 115 of the pusher 110 contacts the posterior wall of the trachea 101, the motion of the first everting film sheath 120 impels it caudally along the tracheal axis without applying a significant force transverse to the tracheal wall.

After the film sheath 120 is fully everted from the pusher 110, the pusher 110 is removed as shown in FIG. 1d and a conventional tracheal tube 103 may be inserted through the film sheath 120 into the trachea 101 as shown in FIG. 1e and connected to, or reside within, the connector 139. Alternatively, the pusher 110 itself may be designed to operate as a tracheal tube. In that case, it may be advantageous to allow a portion of the film sheath to remain inside the pusher 110, preferably attached at its proximal end 124, so that both the outside of the pusher 110 and at least a portion of the inside of the pusher are encased in the film sheath 120, and protected from biofilm, while in use. It will be understood that additional features could be added to any of these embodiments, including, for example, a cuff.

Figure 13:
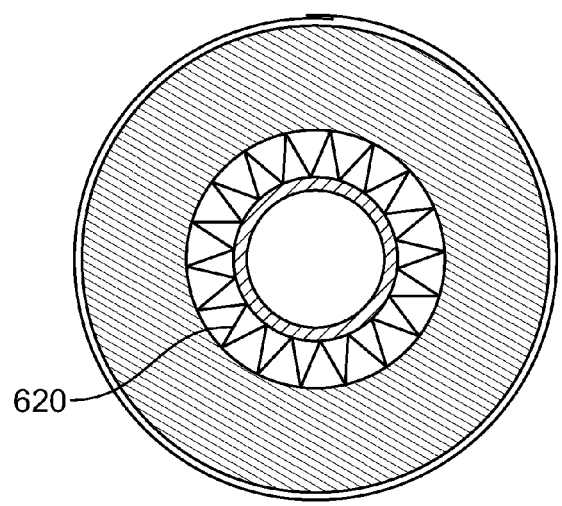
FIG. 13 shows a means of packing the everting film sheath in the lumen of the pusher.

If the conventional tracheal tube 103 includes an inflatable cuff 105 at its distal end, the diameter of the film sheath 120 must be sufficient to pass the deflated cuff 105 and its inflation means without impeding the placement motion. In this case the length of the film sheath 120 is such that its proximal end 124 terminates above the cuff 105 as shown; however, it may be desirable to allow for the distal end of the film sheath 120 to terminate below the cuff 105, forming a protective lubricious barrier between the tracheal tube 103 and cuff 105 and the patient's tissue. In such case, as shown in FIG. 13, the diameter of the film sheath 120 must be wide enough at the point where it covers the cuff 105 to accommodate inflation of the cuff, and the film 620 that ultimately everts to create the wider portion of the sheath 120 may need to be "bunched" or folded longitudinally for storage. It will also be noted that conventional practice requires testing of the cuff before insertion into the trachea. Thus, the guide would optimally include an enlarged or cutaway section to accommodate inflation of the cuff during the test, which is further described below in the text associated with FIG. 6.

Further, since the pusher 110 lays down the film sheath 120 as it advances, dragging against tissue is essentially eliminated such that bacteria, cells, and cellular debris are not tracked from the skin into the wound or trachea as may occur with standard tracheal tube insertion methods.

Biofilm 106 will collect on any foreign object in the trachea, such as a tracheal tube, forming large colonies of bacteria which can lead to local and, ultimately, systemic infections. However, the lubricious fluoropolymer material of the film sheath 120, including, for example, PTFE D/W 200, is resistant to biofilm adhesion. Although some buildup may occur, the colonies are usually shed when they are small and before they can cause infection.

Figure 1F:
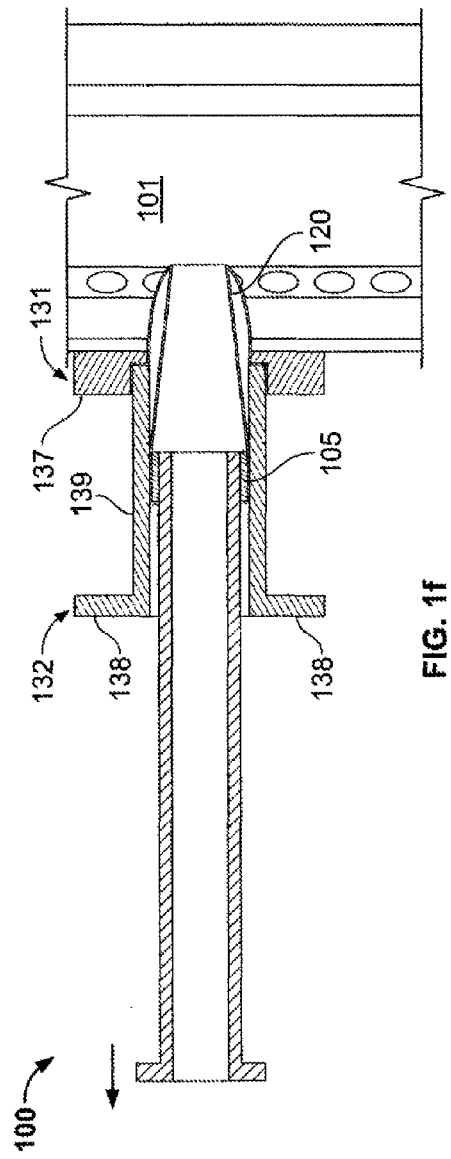

The film sheath 120, which covers the outside portion of the tracheal tube 103, prevents biofilm from collecting on most of the outside portion of the tracheal tube 103 and provides an outward facing biofilm resistant surface. The inside of the tracheal tube 103 will still collect biofilm, but acceptable standard methods of cleaning the inside of the tracheal tubes currently exist, including the use of brushes and replacement of an inner cannula. As shown in FIG. 1e, upon removal of the tracheal tube 103, the closely fitting proximal end 124 of the film sheath 120 is preferably trapped behind the deflated cuff 105, and the film sheath 120 reverts upon tracheal tube 103 removal as shown in FIG. 1f. Unlike conventional removal of a tracheal tube, the biofilm is generally not scraped off and deposited in the trachea and stoma wall during removal, thus reducing the potential of contamination and infection.

The device may be modified to include an integrated tracheal tube 210 as shown in FIGS. 2a and 2b. The pusher 110 is positioned inside the integral tracheal tube 210, but the proximal ends 111 and 211 of the pusher 110 and integrated tracheal tube 210, respectively, are structured for simultaneous movement when the operator's fingers apply force in the manner described above in connection with FIG. 1. In the embodiment shown this is achieved by causing the proximal end 111 of the pusher 110 to have a stand-off edge 214, which may function as a thumb rest, that is wider than the opening to the lumen at the proximal end 211 of the integrated tracheal tube 210, although other designs are possible. The integrated tracheal tube 210 fits inside the guide 130. The distal end 215 of the tracheal tube 210 terminates before the tapered nose 115 of the pusher 110, and may itself be tapered to allow for easier insertion.

In operation, the film sheath 120 emerging from the nose of the pusher 110 everts over both the pusher 110 and the integrated tracheal tube 210 as shown in FIG. 2b. The pusher 110 and the first everting film sheath 120 thereby direct and facilitate the placing of the integrated tracheal tube 210 through the stoma 102 into the tracheal lumen integrally. Both pusher 110 and integrated tracheal tube 210 are flexible and may have a pre-formed curvature memory that causes them to move caudally as they emerge from the guide 130, as described previously in the text associated with FIG. 1, and to conform to the angle between the axes of the stoma 102 and trachea 101 after placement. Accordingly, the identity and function of the pusher 110 and film sheath 120, and the process of placing the film-encased integrated tracheal tube 210 into the trachea 101, are very similar to those described for the identity and function of these components in placing a film sheath 120 alone through an existing stoma 102 as shown in FIG. 1 during the placement of the conventional tracheal tube 103. After full placement of the integrated tracheal tube 210 and removal of the pusher 110, the advantages of a film-encased integrated tracheal tube 210 and film reversion during removal are obtained as illustrated in FIGS. 1e and 1f. FIGS. 2a and 2b show placing of an integrated tracheal tube 210 without a cuff for clarity, but a cuff could be employed with this embodiment of the invention.

The device 100 may also be modified to include cutting means that would allow for percutaneous insertion of the tracheal tube into a patient without a pre-existing stoma or a stoma newly created by conventional means. FIG. 3 shows an embodiment of the device 100 that can be percutaneously placed in the trachea in the process of placing the film sheath 120. The device includes a cutting means, an embodiment of which is shown in detail in FIG. 4, located within the lumen 125 of the pusher 110 and within the portion of the film sheath 120 stored there. The cutting means may be a cutter 301, preferably comprising a sharp point 311 and three or more blades 320 mounted on the distal end 305 of a support member 310 that has an appropriate diameter and shape to fit within the lumen 125. It will be understood that other arrangements of the blades and cutter forms could be used, and it might be desirable to include an opening through the cutter to allow for the use of a guide wire as further described below. As an alternative, for example, the cutter and member could be integrated, as with a guide needle 410 shown in FIGS. 5 through 9. The member 310 or needle 410 may be pushed forward by the operator to extend through the nose 115, cutting the desired tissue, and then withdrawn back into the lumen 125 when no longer needed.

The incision, either as created by the arrangements of blades 320 in a star-like shape or as created by the needle 410, allows for entry of the nose 115 of the pusher 110 into the patient. The first everting film sheath 120 then stretches the skin open radially and allows the nose 115 to proceed into the underlying tissue by blunt dissection. Everting blunt dissection minimizes trauma and bleeding since it is accomplished by spreading the affected tissue rather than by cutting it, and further minimizes the axial force required to spread the tissue. When the spreading action of the first everting film sheath 120 is sufficient to permit progress by blunt dissection, the cutting means may be retracted into the pusher 110. If a non-spreading tissue structure is encountered which does not permit blunt dissection, as might possibly be encountered at or near the tracheal wall 330, the cutting means may again be deployed to initiate the spreading action of the first everting film sheath 120 through that structure. In normal patients, however, additional cutting should not be necessary since the radial stretching action of the first everting film sheath 120 causes tissues that do not spread to be pushed aside rather than being penetrated, for example when the cartilaginous rings in the trachea wall 330 are encountered.

FIGS. 5a-e, 6a-g, 7, 8, 9 and 10 show different views of an embodiment of the current invention that include a pusher 110, film sheath 120, guide 130, and an integrated tracheal tube 210. In the embodiment, a needle 410 is employed as the cutting means, but it will be understood that an alternative cutting means, such as the blades described in connection with FIGS. 3 and 4, could be substituted. In this embodiment of the device, the guide 130 includes a removable stand-off guide 460 with projections B and D. Finger rests 138 which are attached to or integral with the guide 130, preferably as part of the stand-off guide 460, although they might also be integral with the connector 139, function as projections E. The proximal end 411 of the needle 410 includes a projection A; while the proximal end of the pusher 111 includes a projection C. The projections allow for operation of the device with one hand. It will be understood, however, that the projections described are optional, and that the steps described in connection with the projections A through E could instead be performed using more conventional methods. It will also be understood that for ease of use the projections could be located at different angles relative to the longitudinal axis of the device 100 and to each other and could be shaped to conform comfortably accommodate the operator's fingers.

To operate the embodiment shown in FIGS. 5 and 6, after properly positioning the device 100 on the neck over the trachea 101, which may be accomplished using devices and methods described in connection with FIGS. 25 and 26 below, the operator advances the guide needle 410 through the patient's tissue into the trachea 101 by squeezing projections A and B together with the thumb and forefinger from the position shown in FIGS. 5a and 6a to the position shown in FIGS. 5b and 6b, respectively. Detail of the guide needle 410 movement is shown in FIGS. 7 and 8. The distance advanced into the trachea is limited by the standoff at projection B.

Because the distance between the surface of the skin and the trachea tissue can vary significantly between patients, it would be advantageous to be able to appropriately adjust the distance the guide needle 410 moves when projections A and B are squeezed together. This could be accomplished by providing marks on the guide 130, or more preferably by providing small protrusions with detents that provide quantum "clicks" of movement corresponding to a known distance, such as a millimeter. It will be understood that with such a modification the projections A and B might not be brought completely together. Before the procedure, an ultrasound could be performed at the insertion site to determine the depth of the tracheal tissues. The projections A and B would then be brought together a distance equal to the measured depth, plus an additional amount, on the order of a few millimeters, to ensure that the distal end 412 of the guide needle 410 enters the tracheal lumen 101.

In addition, whether or not the penetration of the needle 410 is adjusted, the penetration into the trachea 101 may be verified by a bronchoscope in the trachea 101 as is used in conventional percutaneous dilational tracheostomies.

Figure 5C:
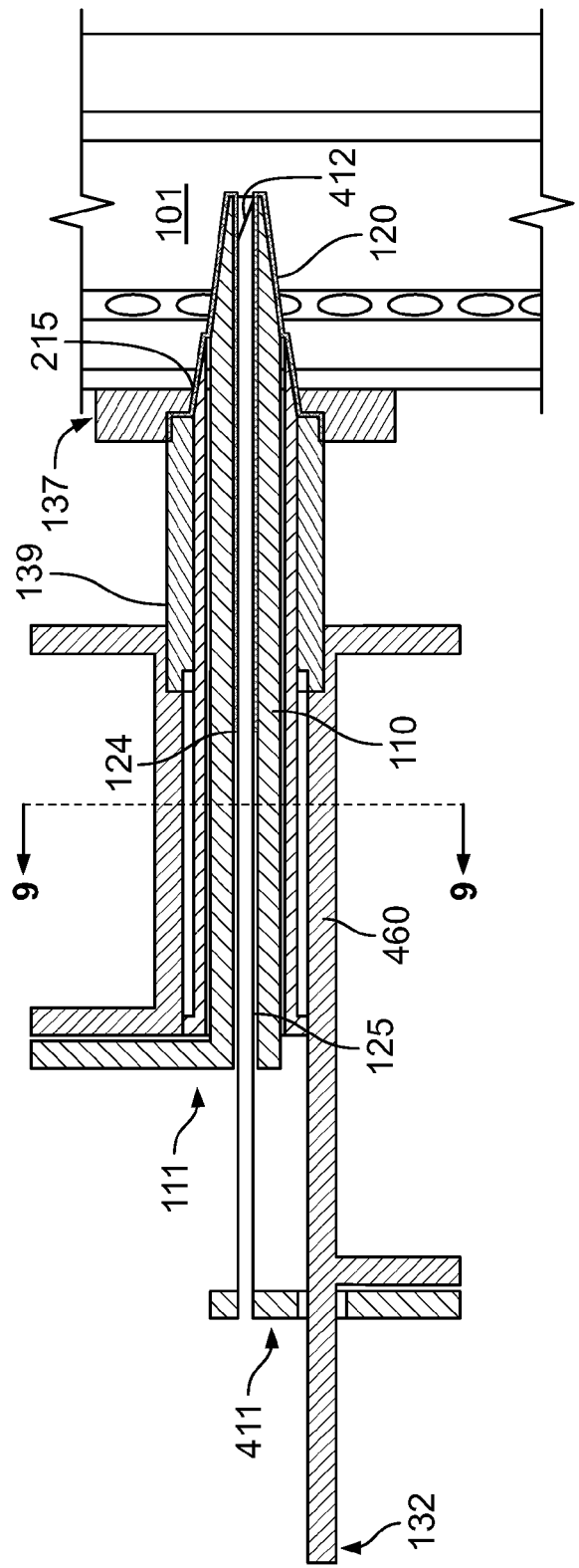
FIGS. 5 *a-e* show in cutaway a preferred embodiment of the current invention suitable for placing film and an integrated tracheostomy tube percutaneously into a patient and illustrate the method steps for placement of the film and tracheostomy tube using dilation and blunt dissection.
Figure 5D:
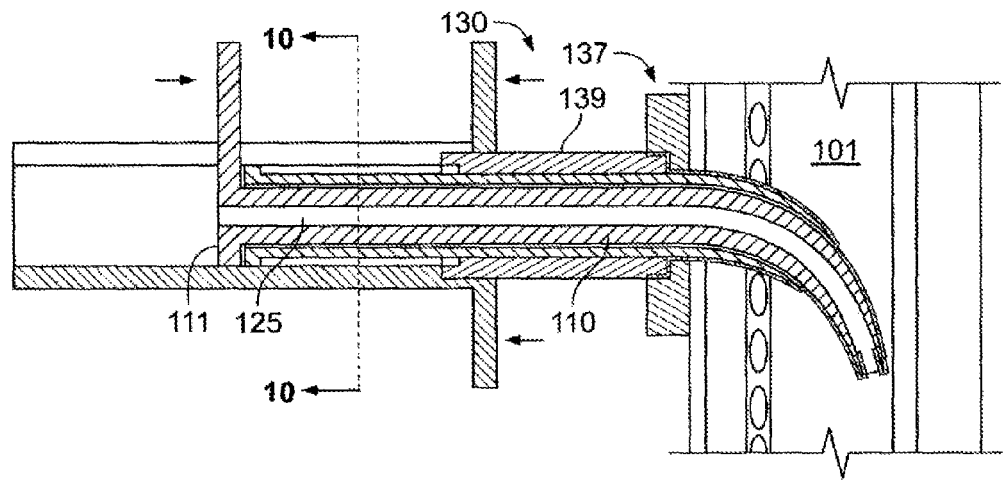

Next, the pusher 110 is advanced by the operator over the guide needle 410 into the trachea by squeezing projections C and D together with the thumb and forefinger to the position shown in FIG. 5c. The distance advanced into the trachea is limited by the standoff at projection D. As previously described, the wound is dilated by purely radial force to the diameter of the tapered distal end 215 of the tracheal tube 210 by the advancement of the tapered nose 115 of the pusher 110 under the first everting film sheath 120. Further, as was described in connection with the needle 410, similar structures could be used to adjust the penetration of the pusher 110 by measuring and/or limiting the distance projections C and D are moved together. Similar marks or detents could be employed. The pusher 110 would be moved approximately the same distance as the needle 410.

Figure 5E:
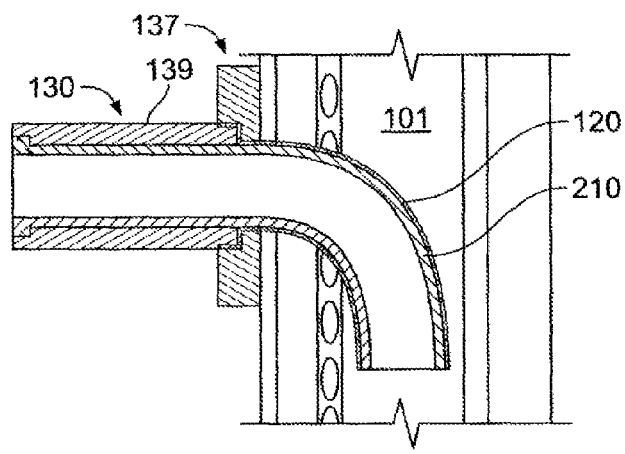
Figure 6C:
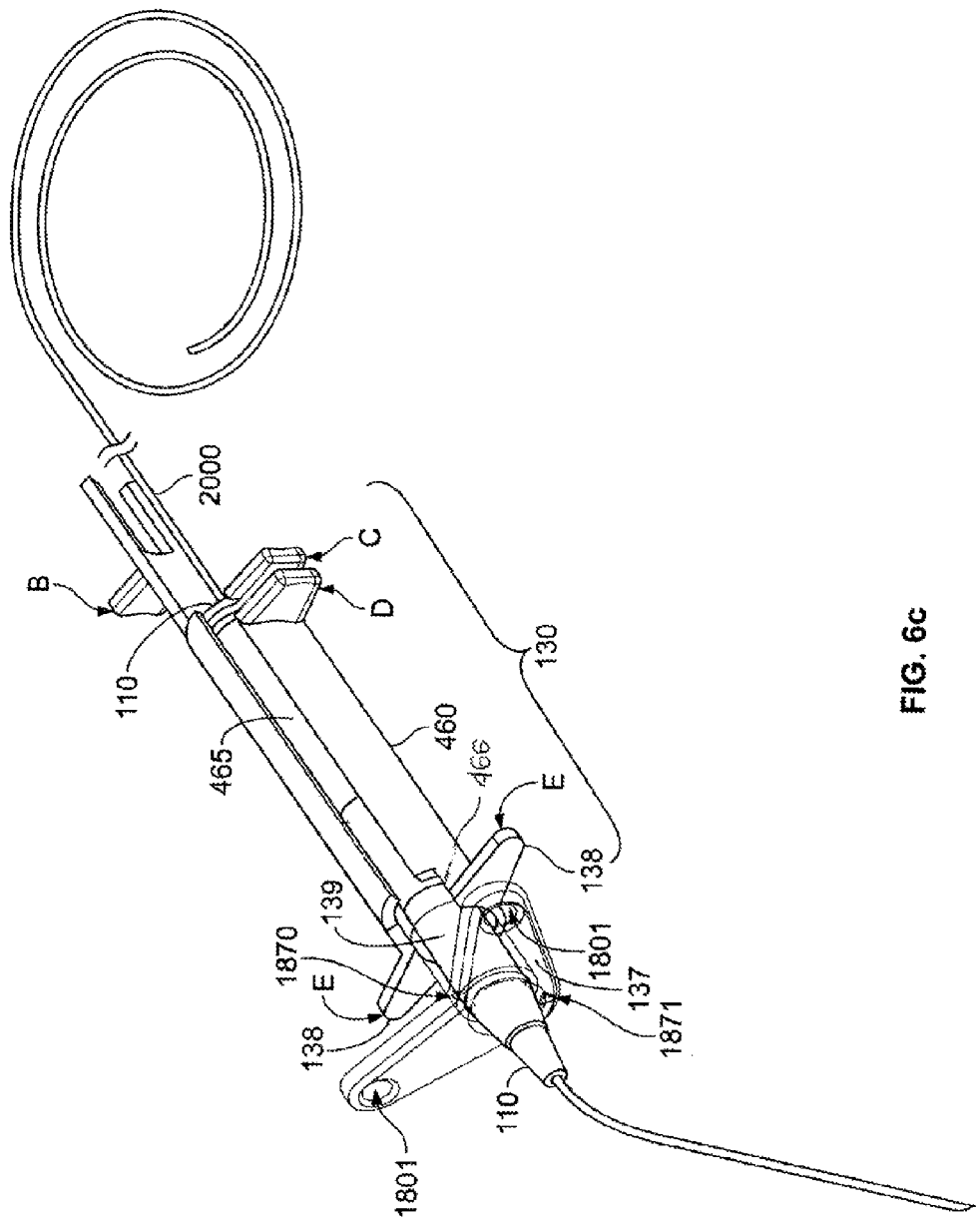
FIGS. 6 *a-g* show a perspective view of a preferred embodiment and steps similar to those shown in FIGS. 5 *a-e*, with additional detail and including the use of a guide wire.
Figure 6D:
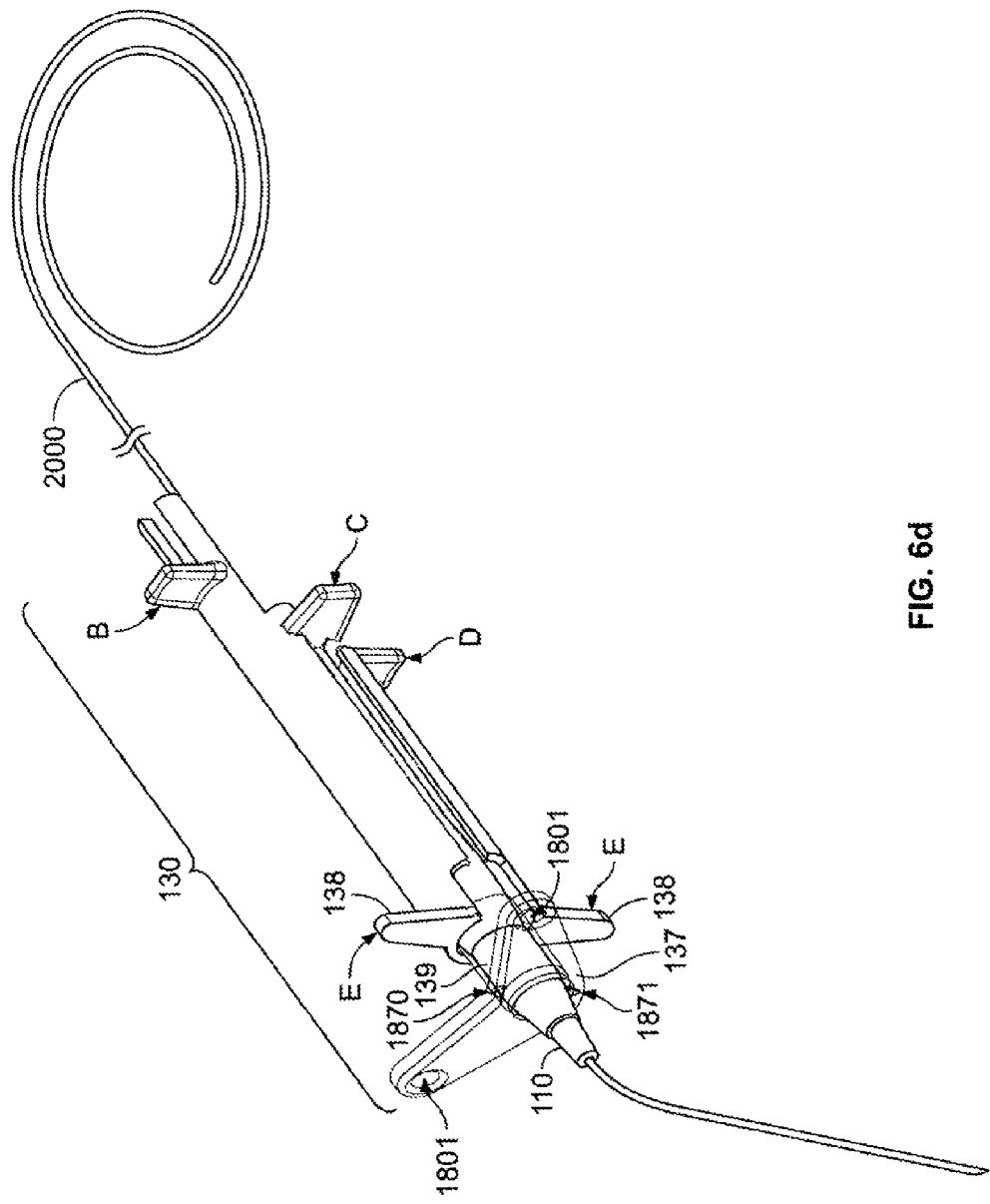
Figure 6E:
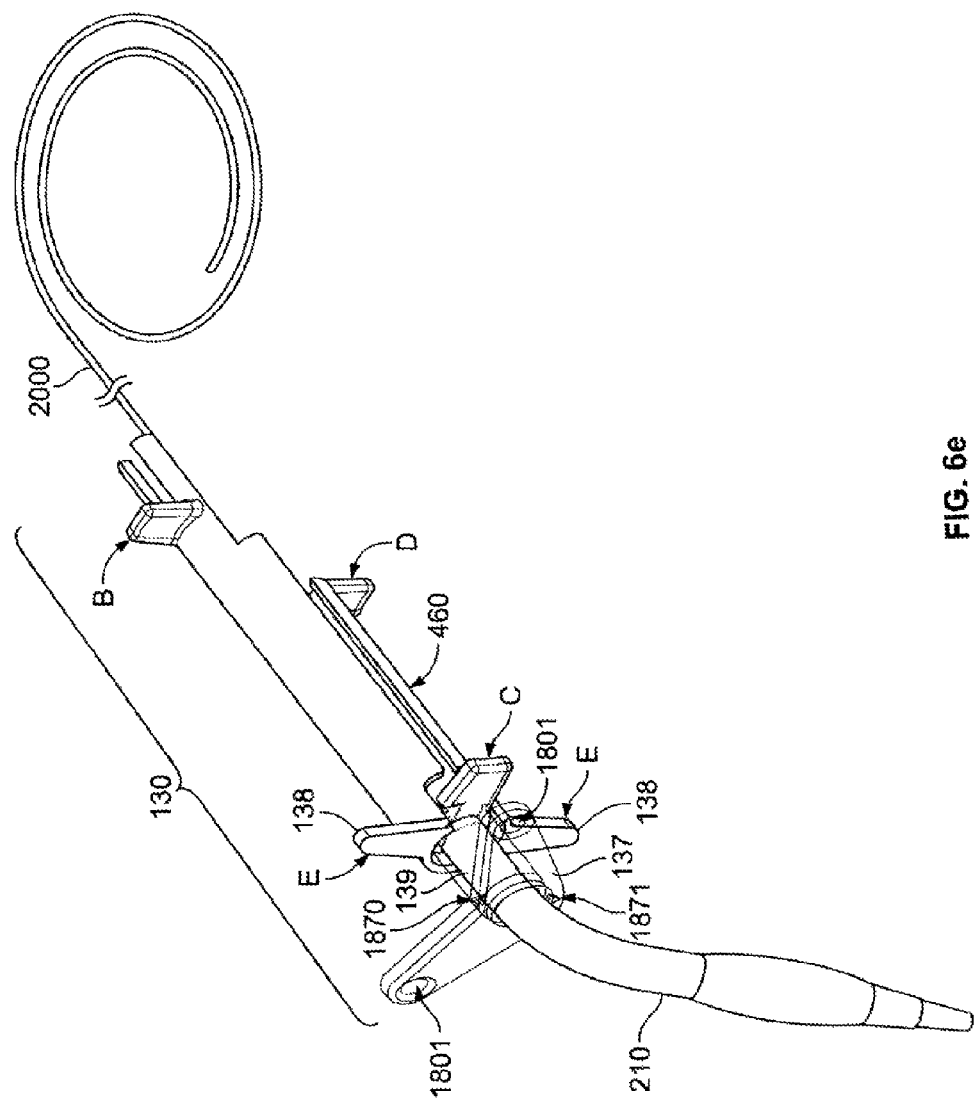
Figure 6G:
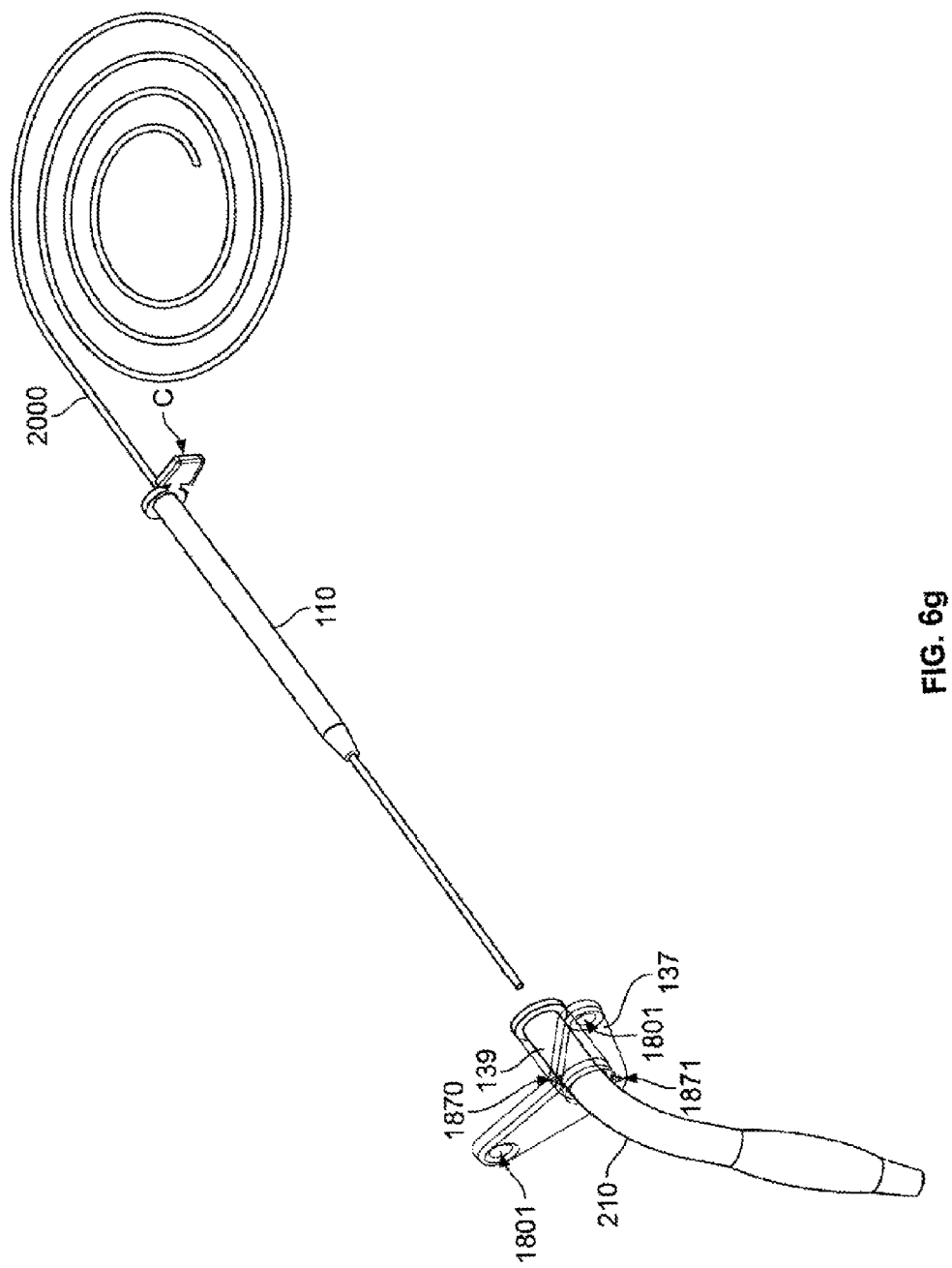
Figure 9:
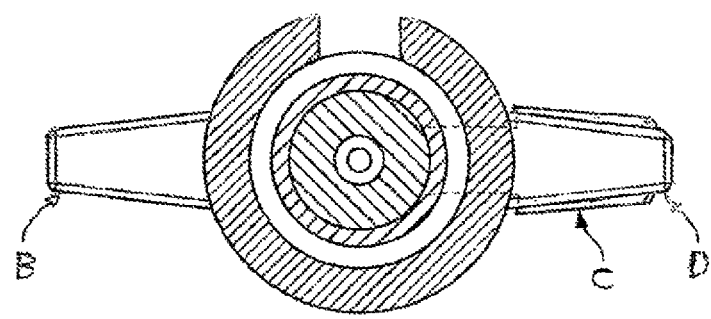
FIG. 9 shows a cross-sectional view of the device position shown in FIG. 5*c*.
Figure 10:
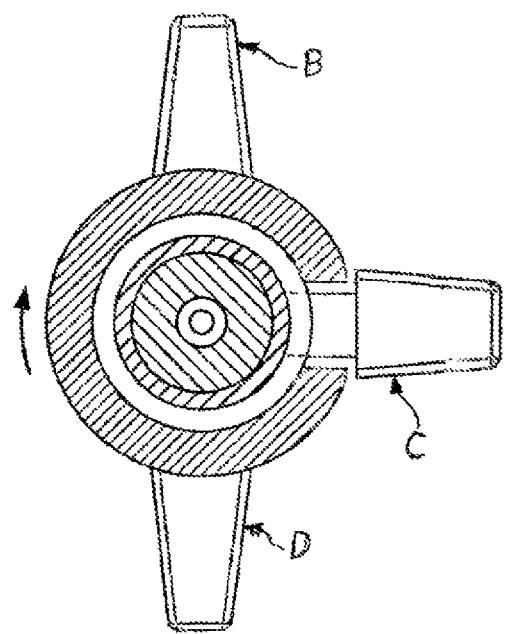
FIG. 10 shows a cross-sectional view of the device position shown in FIG. 5*d*.

The guide needle 410 is then removed. The standoff guide 460 may be removed or, alternatively as shown, may be constructed with a slot having a narrow portion 465 beginning at the proximal end 132 of the guide 130 and extending toward the distal end 131 of the guide 130, and a wider portion 466 near the distal end 131 of the guide 130 so as to allow Projection C at the proximal end 111 of the pusher 110 to be relocated by twisting the standoff guide 460 around the pusher 110, so that Projection C is positioned to move along the narrow portion of the slot 465, as shown in FIGS. 6*d*, 9 and 10. It will be noted that the Projection C may also be removable and, if so, could be removed before advancement of the pusher, thus eliminating the need to rotate the standup guide. The pusher 110 and integral tracheal tube 210 are then advanced fully by squeezing the proximal end 111 of the pusher 110 and the finger rests 138, here shown as projections E, on the proximal end 132 of the guide 130 between the thumb, index and middle fingers in the manner of hypodermic syringe similar to that previously described in connection with FIG. 1, resulting in the structures shown in FIGS. 5*d* and 6*e* and the everted film sheath 120 covering the integrated tracheal tube 210. It should be noted that the film sheath is not shown in FIG. 6 to allow the integral tracheal tube 210 to be more clearly seen. If not previously removed, the stand-off guide would be removed at this time, as shown in FIG. 6*f*. Alternatively, pusher 110 and guide wire 2000, the use of which is further described below, can be first removed followed by removal of the standoff guide 460. After removal of the pusher 110 and guide wire 2000, the integrated tracheal tube 210 becomes fully functional as shown in FIGS. 5*e* and 6*g* with the advantages of being clad in a film sheath as described previously in this document.

Figure 11A:
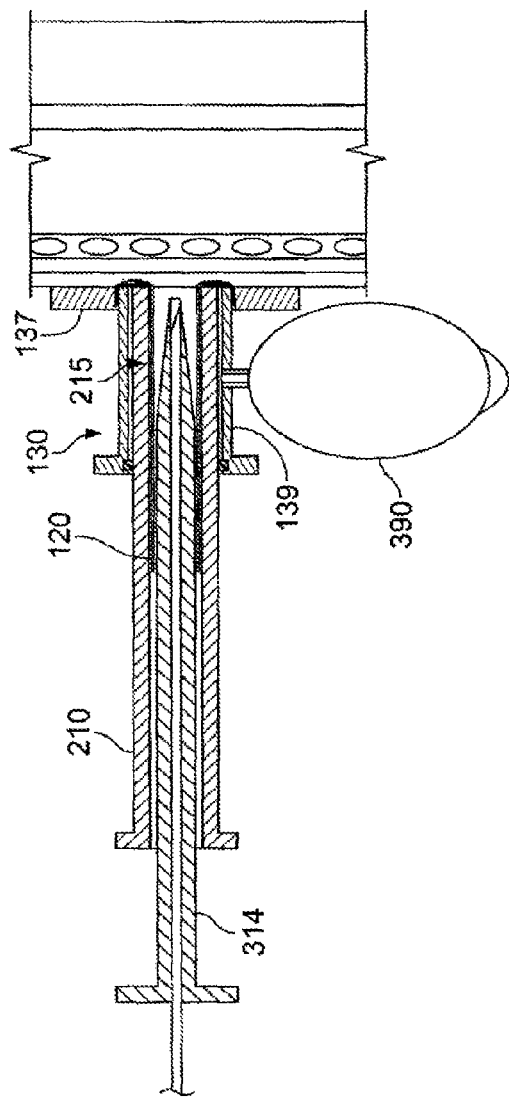
FIGS. 11 a-f show an embodiment of the current invention including a trocar and utilizing the everting film to effect dilation and blunt dissection.
Figure 11B:
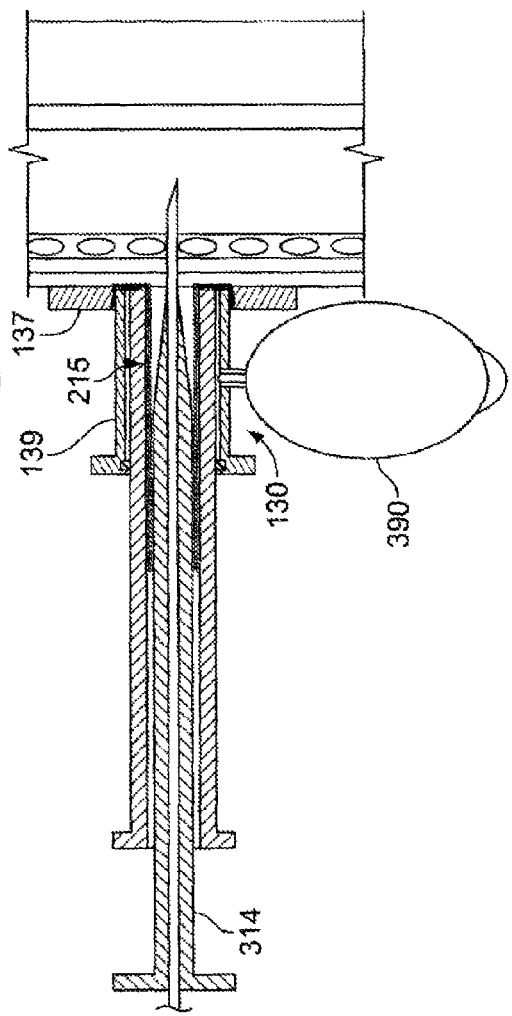
Figure 11C:
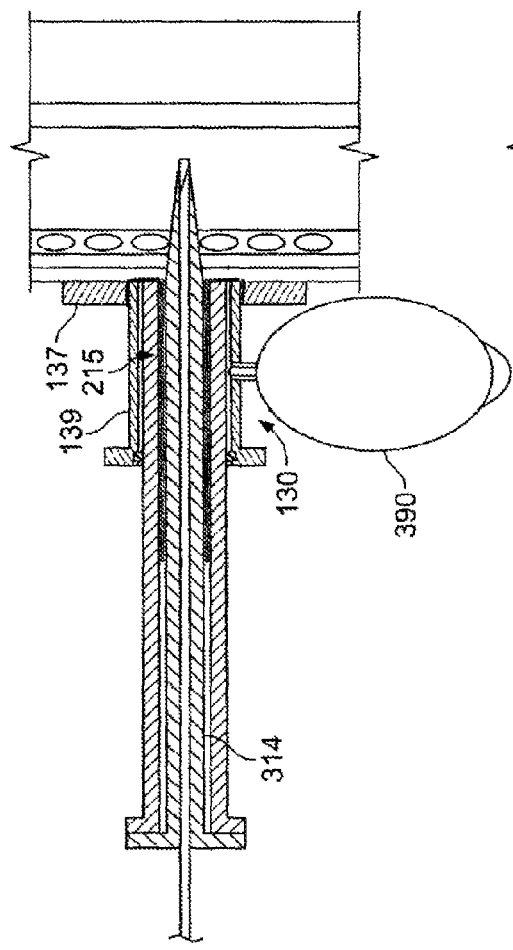
Figure 11D:
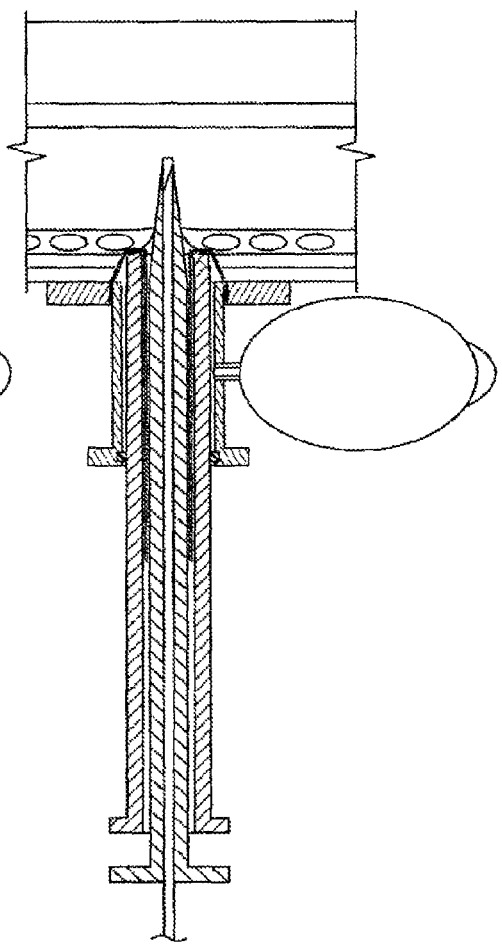
Figure 11E:
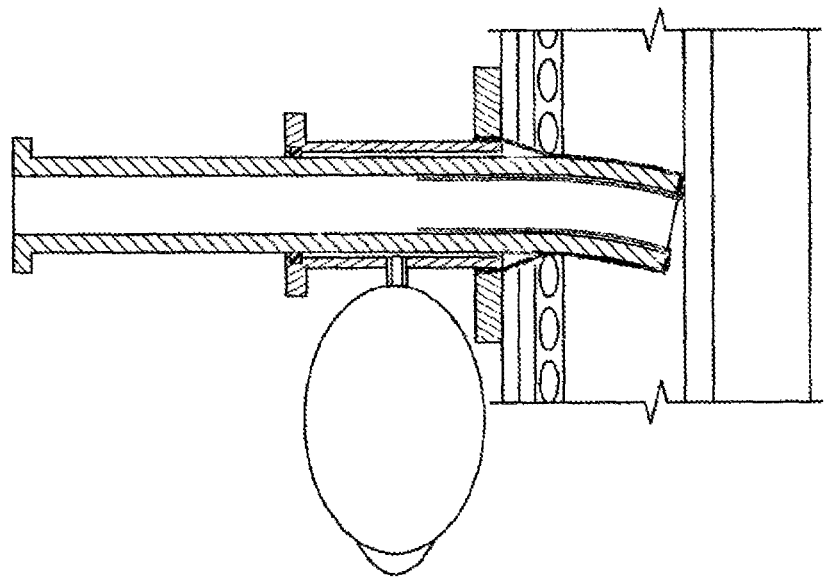
Figure 11F:
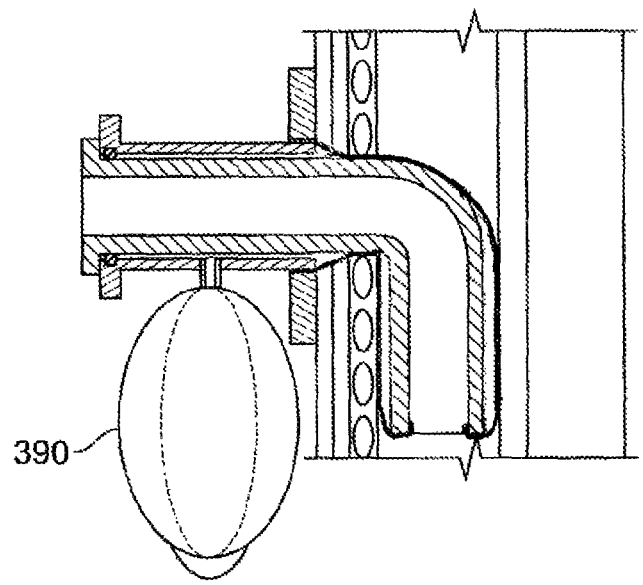

While the above discussions assume a separate pusher that contains the everting film, other forms of pushing means are possible. For example, the tracheal tube itself may perform the pushing function as shown in FIGS. 11*a*-11*f*. As shown in FIG. 11*a*, the film sheath 120 is stored in the lumen of the integrated tracheal tube 210 rather than in a dedicated pusher. The distal end 123 of the film sheath 120 is attached to the guide in one of the manners described above. However the proximal end 124 of the film sheath 120 may be attached to the distal end 215 of the tracheal tube 210 forming an air tight seal. A sliding tapered trocar 314 is contained within the tracheal tube 210. The tapered trocar 314 may be a cutting means or may include cutting device (not shown) at its tapered tip or may contain another cutting means such as a hollow needle or similar penetrator. Once the patient's skin is cut by the cutting means as shown in FIG. 11*b*, the cutting means-initiated opening is enlarged by blunt dissection by advancing the trocar 314 as shown in FIG. 11*c*. The tracheal tube 210 can then be advanced over the trocar 314 everting the film sheath 120. It will be noted that the tracheal tube 210 preferably includes rounded edges on the opening of its distal end 215. The everting process further expands the opening by blunt dissection. After the distal end 215 of the tracheal tube 210 is advanced to be within the trachea of the patient, the trocar 314 is removed and the tracheal tube 210 is advanced further into the trachea. If the proximal end 124 of the film sheath 120 is attached to the distal end 215 of the tracheal tube 210, a film inflation means, such as a film-inflating bulb 390 or syringe, in operable attachment to the guide 130 may be used to inflate the film sheath 120, sealing the space between the trachea and the tracheal tube 210 and preventing air or other materials from the esophagus from entering the lungs.

Figure 12:
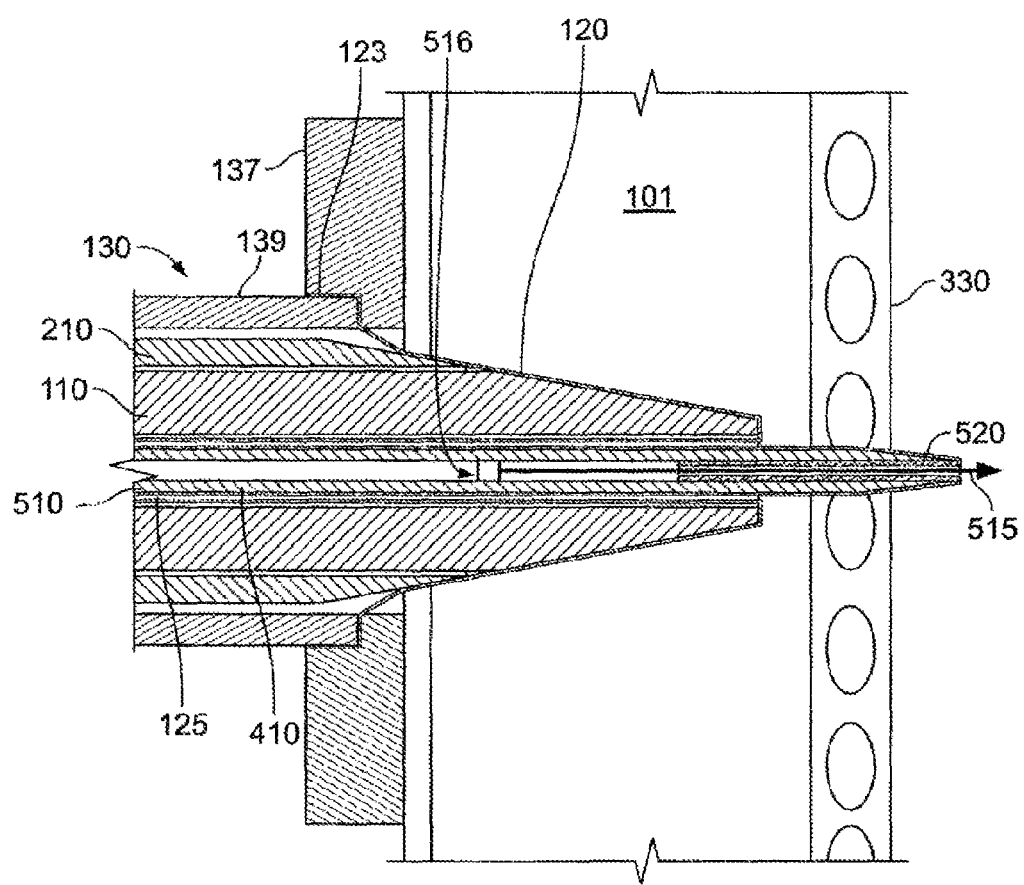
FIG. 12 shows an alternative embodiment of the current invention suitable for percutaneously placing film and a tracheostomy tube utilizing an everting guide needle.

With reference to FIG. 12, the needle may optionally include a separate everting film feature. In this embodiment, rather than the bare needle 410, a hollow everting needle 510, optionally enclosing a sharp-pointed wire 515 or similar device, is employed. In the embodiment shown in FIG. 12, the wire 515 initiates the incision, which is then expanded radially by the needle 510 as it is pushed forward under the everting film 520 by means of blunt dissection in the same manner as the pusher 110 and first everting film sheath 120 expand the incision created by the needle 410. The everting film 520 is initially stored within the needle 510, with one end of the everting film 520 attached to the outside of the needle 510, optimally at or near the proximal end of the needle. The wire 515 may be fixedly attached by means of a holder 516 to the inside of the everting needle 510 as shown, the needle 510 and the wire 515 advancing together being used to initiate the incision. But, alternatively, the wire might be attached to a wire pusher that could be extended from and withdrawn into the everting needle 510 and the nose 115 after use in the same manner that the needle 410 or support member 310 are extended from and withdrawn into the nose 115 and lumen 125 in descriptions of FIGS. 3 and 4. The use of an everting needle 510 has the advantage of creating a wound without the cutting and dragging action of the bare needle 410. Thereafter the everting needle 510 serves the same guide and verification functions as does the bare needle 410 in the embodiment shown in FIGS. 5 and 6 and is similarly withdrawn after serving those functions.

With reference to FIGS. 3, 5, 6, 12 and 14, preferably, the diameter of the nose 115 of the pusher 110 is of only slightly larger diameter than that of the outside diameter of a conventional 14 or 15 gauge hypodermic needle, approximately 0.83 to 0.72 inches. It will be appreciated that the diameter of each subsequent portion of the device to be inserted into the patient should be only slightly larger than that of the previous portion of the device so as to allow for easy advancement through the tissue. Moreover, the tapered ends of the various portions should preferably have rounded edges to decrease the resistance to advancement. However, the minimum inside diameter of the lumen 125 of the pusher 110 and the outside diameter of the needle 510 is limited by the volume required to store the first everting film sheath 120. The volume required to store the film sheath 120 depends on the thickness of the film and the efficiency with which it is packed. In the case where the sheath is longitudinally sealed to form a tube, the volume required to store the film sheath will also be affected by the outside diameter of the pusher or other portion of the device over which it must evert.

The volume needed to store the film sheath can be substantially reduced by more efficiently packing the film to minimize the storage volume it occupies. Conventionally, everting film is formed into a sheath 120 by welding or otherwise sealing the film 620 along its length longitudinally. As shown in FIG. 13, the everting film 620 can then be compressed and bunched up along a particular length in longitudinal folds, and packed axially. This method of packing the film may still be appropriate in certain cases, for example, where a portion of the sheath has a larger diameter than other portions in order to accommodate the inflation of a cuff.

Figure 14:
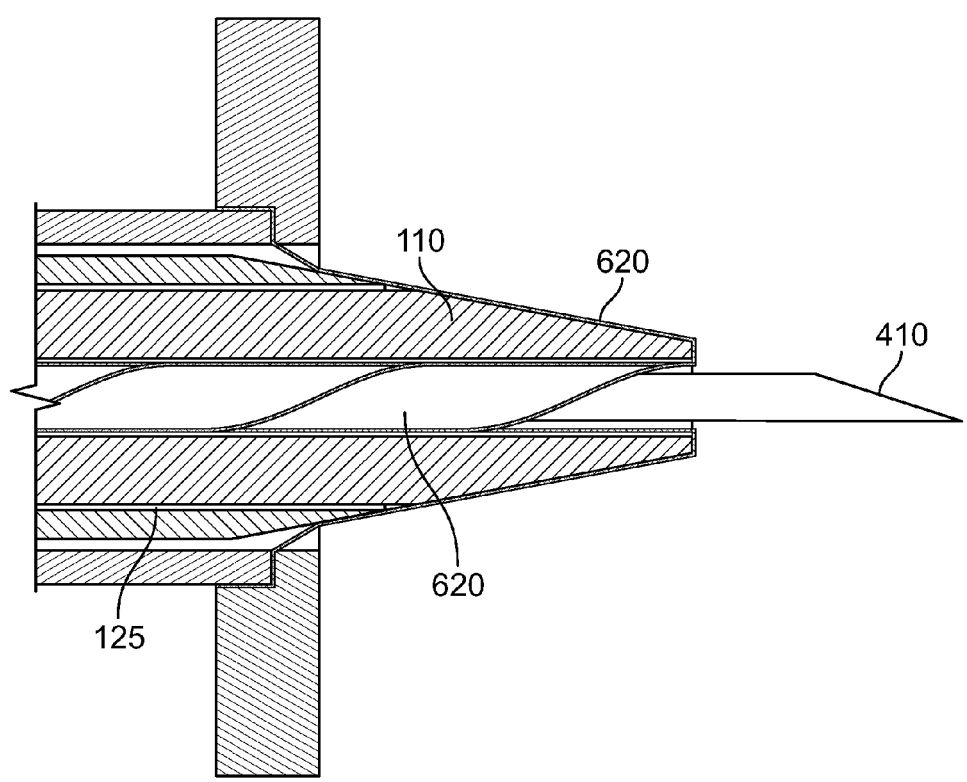
FIG. 14 shows an improved means of packing the everting film sheath in which the everting film is wrapped around a guide needle.
Figure 15:
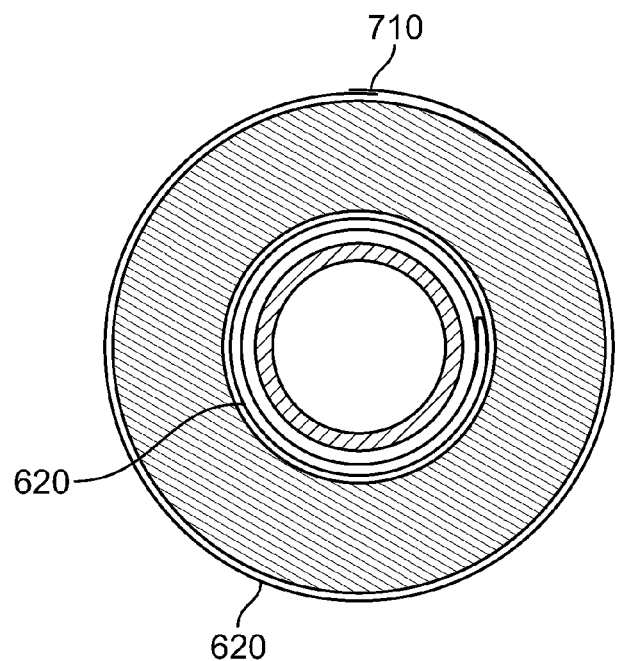
FIG. 15 shows an alternative view of the means of packing the everting film sheath shown in FIG. 14.

However, a more effective way of packing the film 620 is shown in FIGS. 14 and 15 in which the film 620 is wrapped in an axial spiral around a central diameter, such as around the support member 310, the guide needle 410 or the wire 515. However, it may be possible to have the central diameter used only during the manufacturing process and removed, leaving the spiraled film in place in the storage volume. This permits the cross-sectional area, and usually the volume, occupied by the flattened wrapped film in the lumen 125 or similar structure to be significantly reduced. While the embodiment shows the longitudinal edges as welded or sealed together, it will be noted that the edges can be free as described below in connection with FIG. 16.

Figure 16:
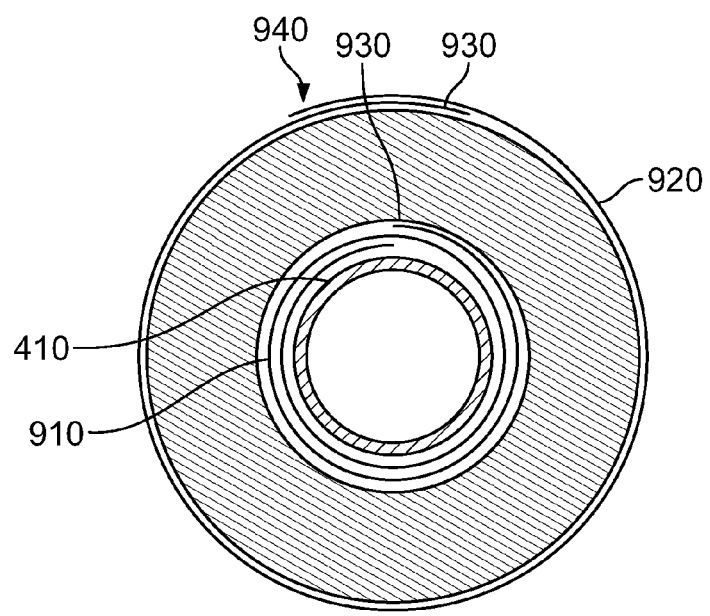
FIG. 16 shows an additional improved means of packing the everting film sheath in which the everting film's longitudinal edges are unconnected and the film is rolled around a guide needle.

As an alternative, with reference to FIG. 16, a flat sheet of film 920 may be rolled around a central diameter as shown at 910. The central diameter may be the guide needle 410 as shown, but may alternatively be the support member 310 in FIG. 3, the guide needle 410 in FIGS. 5 and 6, the trocar 314 in FIG. 11, or any similar structure. As with the axial spiral storage device described above, it may be possible to have the central diameter used only during the manufacturing process and removed, leaving the rolled film in place in the storage volume. The edges of the film 930 are not welded or otherwise sealed, but are designed to overlap 940 when fully everted, thus forming a tubular film conduit, such as the film sheath 120 shown in FIGS. 1 through 6. This structure permits the film sheet 920 to unroll to a much larger diameter sheath without wrinkling as it is everted from the small diameter opening. Also, a rolled film sheath is much easier and less expensive to manufacture than a sheath comprising a sealed film conduit, which requires welding together the edges of a film sheet. The elimination of welding is especially advantageous in the manufacture of the smallest film sheaths for which specialized materials and high precision welding is required and the volume occupied by the welded seams and their stiffness become limiting factors for minimum diameter of the eversion system. The elimination of the welding or bonding is also advantageous in that there is no weld or bond to fail or leak.

It will be appreciated that while in the basic embodiment shown the proximal end 124 of the film sheath 120 is open and the film is attached at the distal end 123 and only attached to the guide 130, for certain applications, including potentially the hollow, everting needle, the proximal end 124 might be attached to the interior lumen of the pushing element to allow for reversion of the film upon removal of the pushing element. Alternatively, in the case where the tracheal tube is the pushing element and a trocar is used, as shown in FIG. 11, the proximal end 124 of the film might be attached to the interior lumen of the pushing element to ensure full containment of the pushing element within the film.

Figure 17:
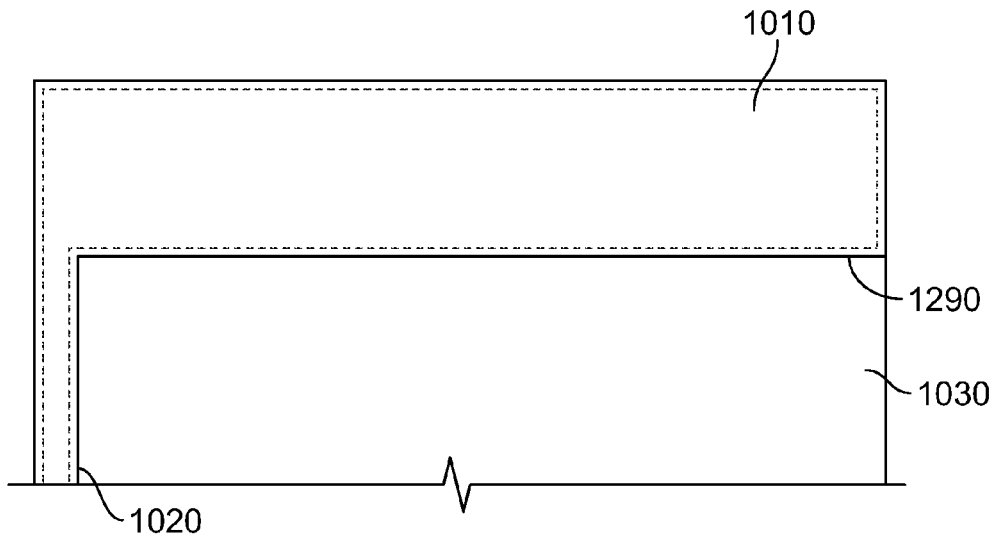
FIG. 17 shows an embodiment of an everting film with an integral inflatable cuff at its distal end.
Figure 18:
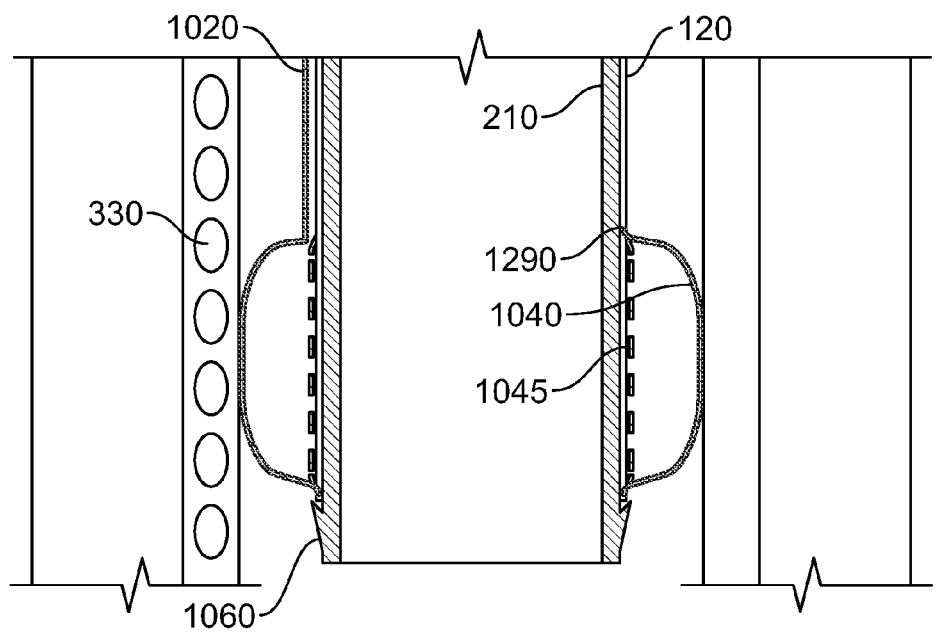
FIG. 18 shows the embodiment of FIG. 17 in use in the trachea.

With reference to FIGS. 17 and 18, the first everting film sheath 120 may optionally include an integrated inflatable cuff at its proximal end shown deflated in FIG. 18 as 1045 and inflated as 1040. A thin elastic film sheet 1010 in the shape of the cuff 1040 and its inflation lumen 1020 are welded 1290 to an inelastic film sheet 1030 composed of the polymer film used to create the film sheath 120 in any of the embodiments previously discussed. The elastic film must have sufficient elasticity to expand to fill the space between the tracheal tube and the trachea wall when forming the cuff, with sufficient strength and minimum thickness to contain the pressure required to inflate it to the required size. Additionally, the elastic film must be biocompatible and stable in the tracheal environment.

Using an inflator bulb, similar to the bulb 390 described in connection with FIG. 11, the cuff can be expanded like a balloon to form an inflated cuff 1040 within the trachea 101 that prevents the flow of ventilator gases from between the outside of the tracheal tube and the tracheal wall and out of the patient's mouth, and prevents the patient from aspirating mucous and material from the esophagus into the lungs. When the cuff is deflated 1045 for removal of the tracheal tube, the elasticity of the deflated cuff 1045 holds the distal end of the inelastic film 1030 of the film sheath 120 close to the outer wall of the tracheal tube 210.

A small ridge or groove 1060 on the outer wall of the tracheal tube, whether integrated as shown as 210, or separate, retains the distal end of the film sheath 120, and the cuff 1040, 1045, preventing it from slipping off the tracheal tube as the tracheal tube is removed. In a manner similar to that shown in FIG. 1ƒ in which the tracheal tube itself has an inflatable cuff, this results in reversion of the film sheath 120, capturing and removing the biofilm that accumulates on the external surface of the film sheath 120 without scraping the biofilm off into the trachea or wound. As a result, infective agents and potential aspirates are not deposited into the trachea during the removal of the tracheal tube.

The elastic film sheet 1010 is positioned at that portion of the inelastic film sheet 1030 intended to eventually form the outwardly facing proximal end 124 of the first everting film sheath 120. The elastic film sheet 1010 is attached to the film sheet 1030 only at the edges, forming the sealed volume required for the cuff 1040 and allowing for the cuff's eventual inflation and expansion. The elastic film sheet 1010 also includes a narrow portion that forms the inflation lumen 1020, which extends longitudinally away from the proximal end 124 of the sheath 120. This portion of the elastic film sheet 1010 is also attached to the film sheet 1030 only at the edges to form a sealed volume connected to the sealed volume that forms the cuff 1040, 1045, and is connected at its distal end to a source of inflation fluid or gas which may be introduced through a passage in the guide 130 or other appropriate means. The inflation fluid or gas used to inflate the cuff can then reach the uninflated cuff 1045 through the inflation lumen 1020.

As suggested above, the cuff 1040, 1045 may be added to any of the embodiments of the film sheath 120 shown above such that the sheath includes both elastic 1010 and inelastic 1030 film sheets. To form a sheath comprising a sealed film conduit, the longitudinal edges of the inelastic film sheet 1030 are welded such that the elastic film 1010 is on the outside of the film sheath 120 when fully everted.

Figure 19:
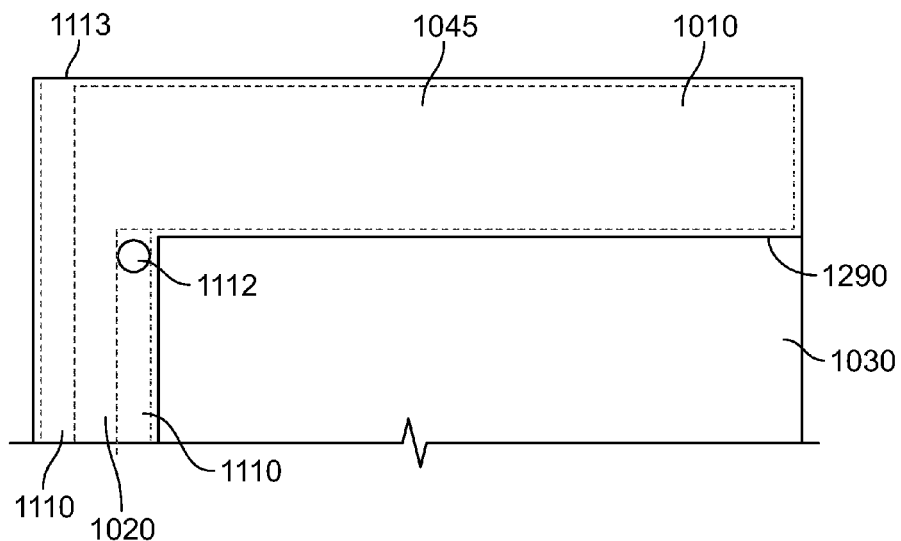
FIG. 19 shows an embodiment of an everting film with an inflatable cuff at its distal end and lumens.

With reference to FIG. 19, it is also possible to create lumens 1110 in addition to the inflation lumen 1020 by attaching the narrower portion of the elastic film sheet 1010 to the film sheet 1030 longitudinally to form multiple channels. The lumens 1110 preferably extend from the distal end 123 of the film sheath 120 to ports 1112, 1113 near the proximal end 124 of the film sheath 120, just above or below the deflated cuff 1045. Such access lumens are useful for passing catheters into the trachea cranially and caudally from the tracheal tube for diagnostic and drug delivery purposes and for inserting suction tubes to remove accumulations of mucous and phlegm or other matter that accumulates above or below the inflated cuff 1040.

With reference to FIGS. 20 to 24, as noted above an important function of the first everting film sheath 120 is to spread tissue, either when entering pre-existing stoma or initiating placement of a tracheal tube percutaneously by blunt dissection. While the lubricious property of the film sheath 120 assists in the eversion process, it decreases the ability of the film sheath 120 to spread tissue. Accordingly, it may be advantageous if the film sheath 120 has a textured exterior surface 1310 where it is intended to engage and spread tissue 1340, while the interior surface 1320 of the film sheath 120 and those portions of the external surface that are not intended to engage tissue retain the lubricious property required by the eversion process.

Figure 20:
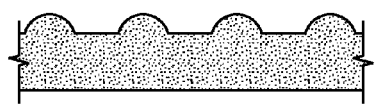
FIG. 20 shows a first example of tissue-engaging film surface structures.
Figure 21:
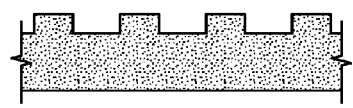
FIG. 21 shows a second example of tissue-engaging film surface structures.
Figure 22:
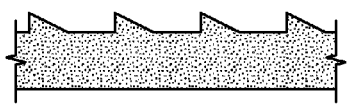
FIG. 22 shows a third example of tissue-engaging film surface structures.
Figure 23:
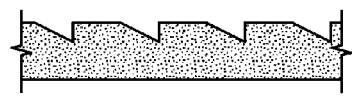
FIG. 23 shows a fourth example of tissue-engaging film surface structures.
Figure 24:
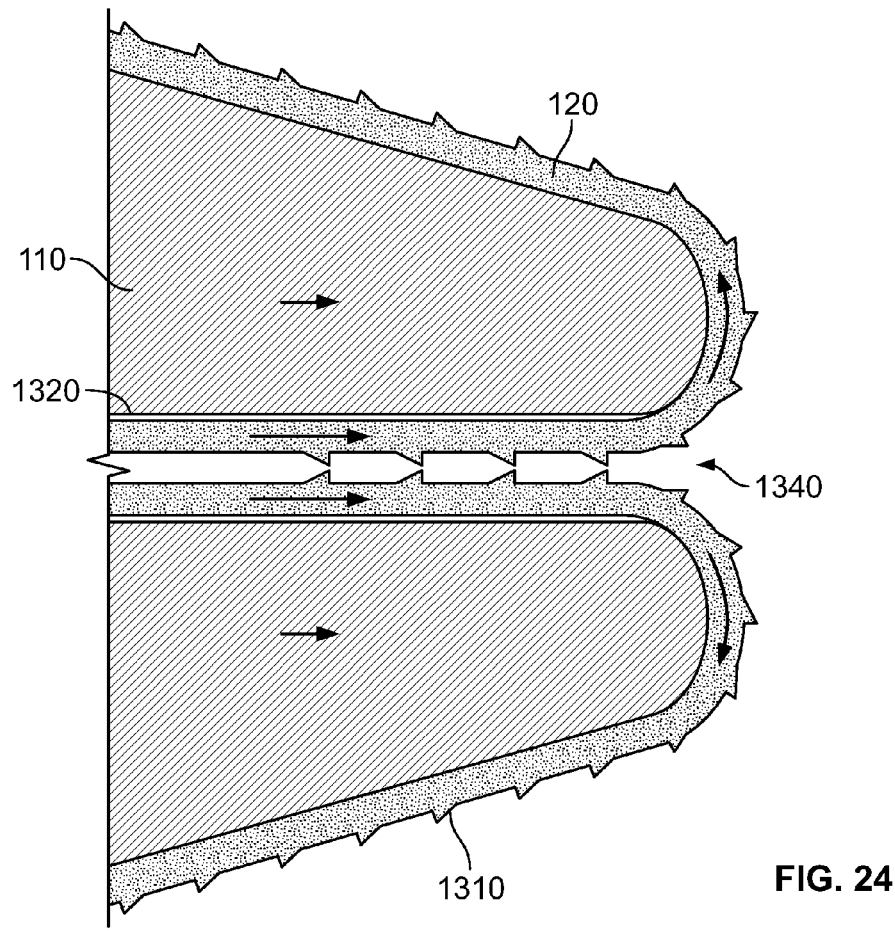
FIG. 24 shows the tissue-engaging film surface structure spreading and dilating tissue by blunt dissection.

The textured exterior surface 1310 can be composed of various alternative tissue-engaging surface features: rounded protrusions as shown in FIG. 20, square-edged as shown in FIG. 21, and sharp-edged as shown in FIGS. 22 and 24. Indentations as illustrated in FIG. 23 may also be used. The textured surface can be formed on the film sheath 120 by molding during formation or by indentation after formation. Persons of ordinary skill in the art will appreciate that other alternative surfaces could be employed; for example, a random variety of surface features can be formed on the film sheath 120 by physical means (e.g., sand blasting), chemical etching, or by engraving by pressing an etched surface against the film sheath 120, or by embedding other materials into the outer surface 1310 of the film sheath 120. Only that portion of the film sheath 120 that engages tissue needs to be textured. It should be noted that while biofilm likely adheres to textured film more than it does to untextured film, generally the size at which the debris sloughs off the textured film is still small enough so as to reduce the potential for infection over use of an unsheathed tracheal tube.

The method of using the current invention requires that the guide 130 be affixed to the patient's neck, correctly positioned over an existing or intended insertion site. Preferably the flange 137 of the guide 130 is shaped to conform to the topography of the neck surface of the patient cranial to the sternal notch and caudal to the thyroid cartilage, and includes means for holding the guide in the correct position on the patient's neck such as a neck strap. As is standard practice, the flange 137 may include holes or slots 1801 designed to accommodate a neck strap (not shown). The neck strap prevents displacement of the guide 130 during the tracheostomy operation and provides support to the devices attached to the flange thus minimizing forces on those tissues in the vicinity of the surgical site. It should be noted that conventional cotton or other fabric neck ties may stretch after being tightened into place, resulting in degradation of function. To avoid this, the neck strap may be configured to resemble an orthopedic collar used to hold the head in a backward-extending, forward-facing position, but adapted to support and properly locate the flange 137 of the device 100 of the invention.

Figure 25:
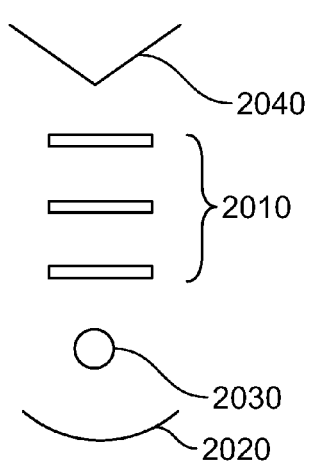
FIG. 25 shows a schematic of the anatomical landmarks and markings on a patient's neck to be used for correctly locating airway access devices.

With reference to FIG. 25, showing a schematic representation of the physiological configuration of a patient's neck, the generally accepted optimum anatomical location of the entrance site axis is perpendicular and directly anterior to the trachea axis between the 1st and 2nd or 2nd and 3rd tracheal rings below the cricoid cartilage 2010, approximately one finger breadth above the sternal notch 2020. When a pre-existing stoma is not present, this location is identified by palpation of the thyroid cartilage 2040 and cricoid cartilage 2010 and, significantly, placing a mark 2030 with a marking pen on the skin at the access site between the 1st and 2nd or 2nd and 3rd tracheal rings.

Figure 26:
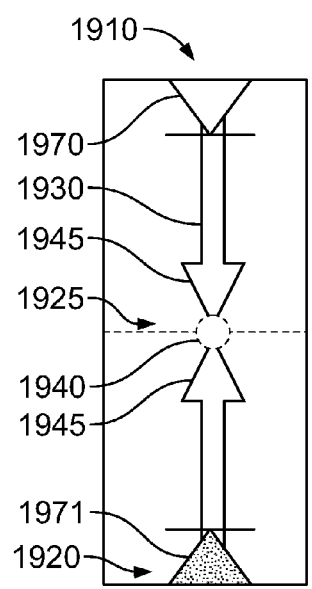
FIG. 26 shows a locator strip to be used to appropriately locate the flange on a patient's neck.

Placement of the guide 130, specifically the flange 137, may be facilitated by the use of a locator strip 1910, shown in FIG. 26. The locator strip 1910, is a strip of temporary, easily-removed, preferably transparent, adhesive tape 1920. The locator strip 1910 includes a hole 1940 marking the location or desired location of the entrance site. The locator strip 1910 includes perforations 1925 transversally at or near its center, preferably through the hole 1940, to allow it to be easily torn apart for removal. The locator strip 1910 has a, preferably heavy, line 1930 adapted to be aligned parallel with the longitudinal axis of the trachea and has arrowheads 1945 or similar indicators pointing to the hole 1940. Upper and lower indicator marks 1970, 1971 are adapted to be easily aligned with corresponding upper and lower guide marks 1870, 1871 on the flange 137 to allow for correct positioning of the device 100.

In addition to reducing tissue trauma and making the insertion of the tracheal tube easier, the current device also allows for a more simplified method of tracheostomy from the current standard of care.

As an example, the method of using the embodiment described in connection with FIGS. 5 and 6 is as follows. It is assumed in this example that the patient has an endotracheal tube and is on a ventilator, but a similar procedure could be used where the patient was not on a ventilator. After preparation of the patient—including sedation, appropriate positioning, and placement on 100% oxygen with appropriate flow—the operator checks the tracheal tube cuff and locates the anatomical landmarks of the patient's neck, all in substantially the same manner as in current procedures. The operator then makes a mark on the patient's skin between the first and second or second and third tracheal rings, approximately one finger breadth above the sternal notch, indicating where the tracheal tube will be inserted. The operator lays the locator strip on the patient's skin, aligning its line parallel with the axis of the trachea and the hole directly over the access site mark on the patient's skin. The flange 137 is then positioned over the locator strip so that upper and lower guide marks 1870, 1871 on the flange match to the upper and lower indicator marks 1910, 1920, respectively, on the locator strip. The neck strap secures the device to the patient, and the locator strip is removed by tearing at the perforations. Use of the locator strip is optional, as those more familiar with percutaneous dilational tracheostomy or this device, may not require its use. At this point in the process, a bronchoscope may be inserted through the endotracheal tube and used in a conventional manner, being withdrawn as a unit with the endotrachael tube until the light from the bronchoscope transilluminates through the skin of the patient at the point where the tracheal tube will ultimately be placed. Finally, the endotracheal tube is reinflated. Conventional adjustments to the respiration would also be made to account for the bronchoscope and any air leak that might occur during the procedure.

The device is then employed as previously described in connection to penetrate the skin and pretracheal tissues, evert the film sheath, and insert the tracheal tube into the patient. After the pusher is removed, the process again follows standard procedures for tracheostomy: the tracheal tube cuff is inflated and the tracheal tube is connected via the connector to appropriate ventilator tubing; and the endotracheal tube and bronchoscope are removed. Preferably, a postoperative chest radiograph is performed to rule out pneumothorax, after which the insertion site may be cleaned and dry dressings applied as needed.

It will be understood that if the device is used for cricothyrotomy the incision might include both a vertical and transverse cut through the cricothyroid membrane, and the procedure could be performed in a non-sterile environment (i.e, in an emergency situation).

Any of the embodiments of the current invention may also be adapted to include a guide wire 2000 which may preferably include a conventional "j" tip. An integral or nonintegral guide wire 2000 may be placed in or reside in the lumen of the needle 410, the pusher 110, or of the trocar 314. The guide wire 2000 may be advanced into the trachea to aid in guiding the pusher 110 and/or the tracheal tube 210 caudally along the tracheal axis. The guide wire 2000 can be advanced after the distal end 115 of the pusher 110 has been advanced to just enter the trachea. If a needle is used, the guide wire 2000 is preferably advanced when the distal end 115 of the pusher 110 is over the tip of the needle 410. Alternatively, the guide wire could be passed down a lumen of the pusher 110 and into the trachea after the needle 410 is removed from the pusher 110, but before the pusher 110, and integral tracheal tube 210 if a part of the device, are advanced fully into the trachea. Use of a guide wire 2000 with a trocar 314 is similarly effected, with the trocar 314 taking the place of the pusher 110. It will be noted, however, that rather than advancing fully into the trachea, the trocar 314 would remain in place while the tracheal tube 210 was initially advanced, to be subsequently removed once the tracheal tube 210 was sufficiently advanced into the trachea. Subsequently, the guide wire 2000 is advanced into the trachea to aid in guiding the tracheal tube 210 caudally along the tracheal axis. The guide wire 2000 would then be removed.

The device allows the surgeon to use the following simplified method for placing a tracheal tube into a patient. It is to be assumed that the patient has an endotracheal tube and is on a ventilator and that the device is as shown in FIG. 6 and includes the use of a guide wire 2000.

1. Sedate patient.
2. Monitor patient's airway pressures, exhaled tidal volumes, and continuous pulse oximetry readings to assure adequate ventilation prior to patient positioning
3. Place patient on 100% oxygen with volume adjusted to compensate for future presence of the bronchoscope
4. Position patient supine with hyperextended neck and support shoulders with a transverse roll (towel or pillow), the head of the patient's bed can be elevated 20 to 30 degrees
5. Perform a screening ultrasound of the neck which may help identify aberrant vessels that may be within the predicted path of the tracheal tube.
6. Verify the integrity of the cuff by inflating it and checking for leaks.
7. Completely deflate the cuff
8. Prep neck and upper chest and drape anterior neck
9. Locate and mark anatomical landmarks: thyroid cartilage, cricoid cartilage, sternal notch
10. Infiltrate incision site with 1% lidocaine with epinephrine
11. Make a mark on the skin between 1st & 2nd or 2nd & 3rd tracheal rings approximately one finger breadth above the sternal notch where access and ultimate tracheal tube placement will be made.
12. Position the device by holding it by the standoff guide with one hand approximately vertical to the patient's neck centering the device flange opening against the skin on the mark previously made at the access site while palpating with a finger of the other hand positioned in the "V" of the flange.
13. Secure the tracheal tube with a neckstrap around the patient's neck.
14. Insert bronchoscope through endotracheal tube and align it.
15. Loosen the tapes of the endotracheal tube and deflate the endotracheal tube cuff
16. Withdraw the bronchoscope and endotracheal tube as a unit until the light from the bronchoscope transilluminates through the skin where access and ultimate tracheal tube placement will be made.
17. Reinflate the endotracheal tube cuff
18. Adjust ventilator tidal volume and frequency as necessary to accommodate the bronchoscope and any air leak that may occur during dilation.
19. While palpating as in step 12 advance central guide needle by squeezing the guide needle and stand-off guide finger rests together, penetrating the skin and pretracheal tissue and entering trachea under direct bronchoscopic visualization by the anesthesiologist/bronchoscopist.
20. Verify entrance of the distal end of the guide needle into the tracheal lumen.
21. Advance the outer coaxial everting pusher and tracheal tube with surrounding film assembly over the guide needle by squeezing pusher and standoff guide finger rests together thus dilating the skin and pretracheal tissue and entering the trachea under direct bronchoscopic visualization. The tip of the assembly will cover the tip of the needle guide.
22. Remove the guide needle over the guide wire.
23. Advance the central guide wire into the trachea to the level of the carina.
24. Rotate the standoff guide such that its slot aligns with the pusher and tracheal tube assembly finger rests.
25. Advance the pusher and tracheal tube assembly over the guide wire by squeezing the pusher and standoff guide finger rests thus fully placing the film covered assembly in the trachea under direct bronchoscopic visualization.
26. Remove the stand-off guide by popping it off the tracheal tube connector.
27. Remove the pusher tube and guide wire.
28. Inflate the tracheal tube cuff
29. Connect the ventilator tubing to the connector of the tracheal tube.
30. Deflate the endotracheal tube cuff and remove the endotracheal tube and the bronchoscope
31. Postoperatively, perform a chest radiograph to rule out pneumothorax
32. Clean the site with sterile saline
33. Apply dry dressings as needed.

While the present invention has been shown and described with reference to the foregoing embodiments and methods, it will be apparent to those skilled in the art that changes in form, connection, and detail may be made therein without departing from the spirit and scope of the invention as defined in the appended claims.

We claim:

1. A medical device for establishing an airway in a patient comprising:
    a guide, said guide defining a first end adapted to be placed and, during operation of the device, remain on the outer skin of a patients neck at an appropriate insertion location for a tracheal tube, and a second end opposite the first end;
    a cutting means for cutting tissue of the patient;
    a pushing means, defining a distal end, a proximal end, a storage space and an opening near the distal end of the pushing means in communication with the storage space; wherein said pushing means is held in moveable relation to the guide such that as the proximal end of the pushing means is moved toward the second end of the guide, the distal end of the pushing means moves away from the first end of the guide;
    a first everting film sheath defining a distal end and a proximal end; wherein a portion of the first everting film sheath is stored within the storage space of the pushing means, a portion of the first everting film sheath near the distal end of the first everting film sheath extends from the opening and is attached near the first end of the guide; whereby as the proximal end of the pushing means is moved toward the first end of the guide, the first everting film sheath everts from the opening; and
    the tracheal tube defining a proximal end and a distal end, held in movable relation to the guide such that as the proximal end of the tracheal tube is moved toward the second end of the guide, the distal end of the tracheal tube moves away from the first end of the guide.

2. The medical device of claim 1 wherein the pushing means comprises a separate pusher.

3. The medical device of claim 2 wherein the pushing means is positioned to lie inside the tracheal tube.

4. The medical device of claim 1 wherein the tracheal tube is the pushing means.

5. A medical device for establishing an airway in a patient comprising:
- a guide, said guide defining a first end adapted to be placed and, during operation of the device, remain on the outer skin of a patients neck at an appropriate insertion location for a tracheal tube, and a second end opposite the first end;
- a cutting means for making an incision in tissue at the insertion location;
- a pushing means, defining a distal end adapted for entry into the incision, a proximal end, a storage space and an opening near the distal end of the pushing means in communication with the storage space; wherein said pushing means is held in moveable relation to the guide such that when the first end of the guide is placed at the appropriate insertion location and the cutting means has made an incision in tissue at the insertion location, as the proximal end of the pushing means is moved toward the second end of the guide, the distal end of the pushing means moves away from the first end of the guide and into the incision;
- a first everting film sheath defining a distal end and a proximal end; wherein a portion of the first everting film sheath is stored within the storage space of the pushing means, a portion of the first everting film sheath near the distal end of the first everting film sheath extends from the opening and is attached near the first end of the guide; whereby when the first end of the guide is placed at the appropriate insertion location and the cutting means has made an incision in tissue at the insertion location, as the proximal end of the pushing means is moved toward the first end of the guide, the first everting film sheath everts from the opening and effects blunt dissection of the tissue at the insertion location; and
- the tracheal tube defining a proximal end and a distal end, held in movable relation to the guide such that when the first end of the guide is placed at the appropriate insertion location and the cutting means has made an incision in tissue at the insertion location, as the proximal end of the tracheal tube is moved toward the second end of the guide, the distal end of the tracheal tube moves away from the first end of the guide and into the incision.

6. The medical device of claim 5 wherein the tracheal tube is the pushing means.

7. The medical device of claim 5 wherein the pushing means is positioned to lie inside the tracheal tube.

8. A medical device for establishing an airway in a patient consisting essentially of:
- a guide, said guide defining a first end adapted to be placed and, during operation of the device, remain on the outer skin of a patient's neck at an appropriate insertion location for a tracheal tube, and a second end opposite the first end;
- a cutting means for making an incision in tissue at the insertion location;
- a pushing means, defining a distal end, a proximal end, a storage space and an opening near the distal end of the pushing means in communication with the storage space; wherein said pushing means is held in moveable relation to the guide such that as the proximal end of the pushing means is moved toward the second end of the guide, the distal end of the pushing means moves away from the first end of the guide;
- a first everting film sheath defining a distal end and a proximal end; wherein a portion of the first everting film sheath is stored within the storage space of the pushing means, a portion of the first everting film sheath near the distal end of the first everting film sheath extends from the opening and is attached near the first end of the guide; whereby as the proximal end of the pushing means is moved toward the first end of the guide, the first everting film sheath everts from the opening; and
- the tracheal tube defining a proximal end and a distal end, held in movable relation to the guide such that as the proximal end of the tracheal tube is moved toward the second end of the guide, the distal end of the tracheal tube moves away from the first end of the guide.

9. The medical device of claim 8 wherein the storage space is a lumen and wherein the cutting means defines a proximal end and a sharp distal end adapted for piercing the tissue of the patient and wherein the cutting means is held in movable relation to the guide such that during operation of the device as the proximal end of the cutting means is moved toward the second end of the guide, the sharp distal end of the cutting means moves away from the first end of the guide.

10. The medical device of claim 8 wherein the tracheal tube is the pushing means.

11. The medical device of claim 8 wherein the pushing means is positioned to lie inside the tracheal tube.

* * * * *